US006984643B2

(12) United States Patent
Du Bois et al.

(10) Patent No.: US 6,984,643 B2
(45) Date of Patent: Jan. 10, 2006

(54) 2,5-SUBSTITUTED PYRIMIDINE DERIVATIVES-CCR-3 RECEPTOR ANTAGONISTS

(75) Inventors: Daisy Joe Du Bois, Palo Alto, CA (US); Long Mao, San Diego, CA (US); Daniel Harry Rogers, San Diego, CA (US); John Patrick Williams, San Diego, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 157 days.

(21) Appl. No.: 10/611,049

(22) Filed: Jul. 1, 2003

(65) Prior Publication Data

US 2004/0014775 A1 Jan. 22, 2004

Related U.S. Application Data

(60) Provisional application No. 60/393,524, filed on Jul. 2, 2002.

(51) Int. Cl.
*C07D 401/12* (2006.01)
*A61K 31/506* (2006.01)
*A31P 11/06* (2006.01)

(52) U.S. Cl. ............... 514/256; 514/274; 514/275; 544/316; 544/332; 544/335
(58) Field of Classification Search ............ 514/256, 514/274, 275; 544/316, 332, 335
See application file for complete search history.

(56) References Cited

U.S. PATENT DOCUMENTS 4,716,166 A * 12/1987 Abou-Gharbia et al. ............................................ 514/263.22

FOREIGN PATENT DOCUMENTS

| EP | 0 640 599 A1 | 8/1994 |
| EP | 1 201 239 A1 | 5/2002 |
| GB | 2 343 893 A1 | 5/2000 |
| WO | WO 97/36875 A1 | 10/1997 |
| WO | WO 97/36901 A1 | 10/1997 |
| WO | WO 00/31032 A1 | 6/2000 |
| WO | WO 00/73278 A2 | 12/2000 |
| WO | WO 01/00617 A2 | 1/2001 |

OTHER PUBLICATIONS

Barnes, Peter J., Ann. Rev. Pharmacol. Toxicol., 2002, 42, 81–98.*
Stella, Valentino J, Expert. Opin. Ther. Patents, 14, 2004, 277–280.*
Wolff, Manfred E. "Buger's Medicinal Chemistry, 5ed, Part 1", John Wiley & Sons, 1995, pp. 975–977.*
Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Barnes PJ., Annu Rev Pharmacol Toxicol. 2002;42:81–98, Medline abstract PMID: 11807165.*
Owen C., Pulm Pharmacol Ther. 2001;14(3):193–202., abstract only.*
Lloyd CM, Rankin SM., Curr Opin Pharmacol. Aug. 2003;3(4):443–8. abstract only.*
Naya, Akira et al., Discovery of a Novel CCR3 Selective Antagonist, *Bioorganic & Medicinal Chemistry Letters*, 2001, pp. 1219–1223, vol. 11, No. 9, Pergamon, Elsevier Science Lld.
Banwell, M.E. et al., "Regulation of Human Eotaxin–3/CCL26 Expression: Modulation by Cytokines and Glucocorticoids", *Cytokine*, (2002) 17(6):317–323.
Barnes, P.J., "Cytokine–directed therapies for the treatment of chronic airway diseases", *Cytokine & Growth Factor Reviews* (2003) 14:511–522.
Ettmayer, P., et al., "Lessons Learned from Marketed and Investigational Prodrugs", *J Med Chem*, (2004) 47(10); 2393–2404.
Kim, Y.J., et al., "Eosinophil–Induced Chronic Hepatitis", *J. Korean Med Sci* (1998) 13:219–222.
Lampinen, M., et al., "Cytokine–regulated accumulation of eosinophils in inflammatory disease", *Allergy* (2004) 59:793–805.
Owen, C., "Chemokine Receptors in Airway Disease: Which Receptors to Target?", *Pulm Pharmacol & Therap* (2001) 14:193–202.
Poulsen, L.K., et al., "Biomolecular Regulation of the IgE Immune Response III. Cytokine Profiles in Atopic Dermatitis, Inhalant Allergy and Non–Allergic Donors", *Cytokine*, (1996) 8(8):651–657.
Radinger, M., et al., "Eotaxin–2 regulates newly produced and CD34* airway eosinophils after allergen exposure", *J. Allergy Clin Immunol* (2004) 113:1109–16.
Rothenberg, M.E., "Eosinophilic gastrointestinal disorders (EGID)", *J Allergy Clin Immunol* (Jan. 2004) pp 11–28.
Shakoory, B., et al., "The Role of Human Mast Cell–Derived Cytokines in Eosinophil Biology", *J Interferon Cytokine Res* (2004) 24:271–81.
Straumann, A., et al., The physiological and pathophysiological roles of eosinophils in the gastrointestinal tract, *Allergy* (2004) 59:15–25.
Webb, D.C., et al., "Distinct spatial requirement for eosinophil–induced airways hyperreactivity", *Immunol Cell Biol* (2001) 79:165–69.
Sabroe, I., et al., "A Small Molecule Antagonist of Chemokine Receptors CCR1 and CCR3", *J Biol Chem*, (2000) 275(34):25985–25992.
White, J.R., et al., :Identification of Potent, Selective Non--peptide CC Chemokine Receptor–3 Atnagonist That Inhibits Eotaxin–, Eotaxin–2–, and Monocyte chemotactic Protein–4–Induced Eosinophil Migration, *J Biol Chem*, (2000) 275(47): 36626–36631.
Ying, S., et al., "Eosinophil Chemotactic Chemokines (Eotaxin, Eotaxin–2, RANTES, Monocyte Chemoattractant Protein–3 (MCP–3), and MCP–4), and C–C Chemokine Receptor 3 Expression in Bronchial Biopsies from Atopic and Nonatopic (Intrinsic) Asthmatics", *J Immunol*, (1999) pp 6322–6329.

* cited by examiner

*Primary Examiner*—Thomas C. McKenzie
(74) *Attorney, Agent, or Firm*—Grant D. Green

(57) ABSTRACT

Compounds of Formula (I):

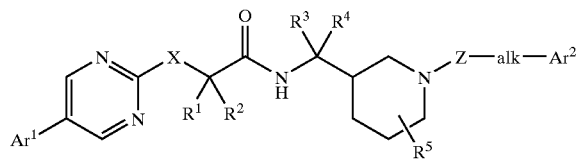

wherein $Ar^1$ is aryl; $Ar^2$ is hydrogen, cycloalkyl, aryl or heteroaryl; Z is —C(=O) or a single bond; $R^1$, $R^2$, $R^3$, $R^4$ and $R^5$ are independently hydrogen or alkyl optionally substituted with hydroxy; alk is an alkylene chain of one to six carbon atoms; X is —O—, —$NR^h$ (where $R^h$ is hydrogen or alkyl), $(CR^6R^7)_m$ (where $R^6$ and $R^7$ are independently in each occurrence hydrogen or alkyl and m is an integer from 0 to 3), or —$S(O)_n$ (wherein n is an integer from 0 to 2); or prodrugs thereof, and pharmaceutically acceptable salts thereof,
are inhibitors of CCR3 useful for treating eosinophil induced diseases such as asthma.

22 Claims, No Drawings

2,5-SUBSTITUTED PYRIMIDINE DERIVATIVES-CCR-3 RECEPTOR ANTAGONISTS

CROSS REFERENCE

This application claims the benefit of priority of U.S. Provisional Patent Application Ser. No. 60/393,524, filed Jul. 2, 2002, which is incorporated herein by reference in its entirety.

FIELD OF THE INVENTION

This invention relates to certain 2,5-substituted pyrimidine derivatives that are CCR-3 receptor antagonists, pharmaceutical compositions containing them, methods for their use, and methods for preparing these compounds.

BACKGROUND INFORMATION

Tissue eosinophilia is a feature of a number of pathological conditions such as asthma, rhinitis, eczema, and parasitic infections (see Bousquet, J. et al. *N. Eng. J. Med.* 323: 1033–1039 (1990) and Kay, A. B. and Corrigan, C. J. *Br. Med. Bull.* 48:51–64 (1992)). In asthma, eosinophil accumulation and activation are associated with damage to bronchial epithelium and hyperresponsiveness to constrictor mediators. Chemokines such as RANTES, eotaxin, and MCP-3 are known to activate eosinophils (see Baggiolini, M. and Dahinden, C. A. *Immunol. Today.* 15:127–133 (1994), Rot, A. M. et al. *J. Exp. Med.* 176, 1489–1495 (1992), and Ponath, P. D. et al. *J. Clin. Invest.*, Vol. 97, #3, 604–612 (1996)). However, unlike RANTES and MCP-3 which also induce the migration of other leukocyte cell types, eotaxin is selectively chemotactic for eosinophils (see Griffith-Johnson, D. A et al. *Biochem. Biophy. Res. Commun.* 197:1167 (1993) and Jose, P. J. et al. *Biochem. Biophy. Res. Commun.* 207, 788 (1994)). Specific eosinophil accumulation was observed at the site of administration of eotaxin whether by intradermal or intraperitoneal injection or aerosol inhalation (see Griffith-Johnson, D. A et al. *Biochem. Biophy. Res. Commun.* 197:1167 (1993); Jose, P. J. et al. *J. Exp. Med.* 179, 881–887 (1994); Rothenberg, M. E. et al. *J. Exp. Med.* 181, 1211 (1995); and Ponath. P. D. *J. Clin. Invest.*, Vol. 97, #3, 604–612 (1996)).

Glucocorticoids such as dexamethasone, methprednisolone, and hydrocortisone have been used for treating many eosinophil-related disorders, including bronchial asthma (R. P. Schleimer et. al., *Am. Rev. Respir. Dis*,. 141, 559 (1990)). The glucocorticoids are believed to inhibit IL-5, IL-3 mediated eosinophil survival in these diseases. However, prolonged use of glucocorticoids can lead to side effects such as glaucoma, osteoporosis, and growth retardation in the patients (see Hanania N. A et al., *J. Allergy and Clin. Immunol.*, Vol. 96, 571–579 (1995) and Saha M. T. et al, *Acta Paediatrica*, Vol. 86, #2, 138–142 (1997)). It is therefore desirable to have an alternative means of treating eosinophil related diseases without incurring these undesirable side effects.

Recently, the CCR-3 receptor was identified as a major chemokine receptor that eosinophils use for their response to eotaxin, RANTES, and MCP-3. When transfected into a murine pre-β lymphoma line, CCR-3 bound eotaxin, RANTES, and MCP-3 conferred chemotactic responses on these cells to eotaxin, RANTES, and MCP-3 (see Ponath. P. D. et al. *J. Exp. Med.* 183, 2437–2448 (1996)). The CCR-3 receptor is expressed on the surface of eosinophils, T-cells (subtype Th-2), basophils, and mast cells and is highly selective for eotaxin. Studies have shown that pretreatment of eosinophils with an anti-CCR-3 mAb completely inhibits eosinophil chemotaxis to eotaxin, RANTES, and MCP-3 (see Heath H. et al. *J. Clin. Invest.*, Vol. 99, #2, 178–184 (1997)). Applicants' co-pending U.S. patent application Ser. Nos. 09/134,013, filed Aug. 14, 1998 and WO 00/31032 discloses CCR-3 antagonists that inhibit eosinophilic recruitment by chemokine such as eotaxin. Therefore, blocking the ability of the CCR-3 receptor to bind RANTES, MCP-3, and eotaxin and thereby preventing the recruitment of eosinophils should provide for the treatment of eosinophil-mediated inflammatory diseases.

The present invention concerns novel pyrimidine derivatives which are capable of inhibiting the binding of eotaxin to the CCR-3 receptor and thereby provide a means of combating eosinophil induced diseases, such as asthma.

SUMMARY OF THE INVENTION

In a first aspect, this invention provides a compound of Formula (I):

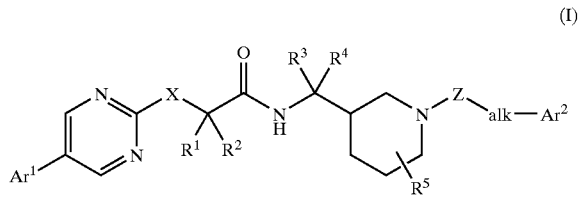

wherein:
  $Ar^1$ is aryl;
  $Ar^2$ is hydrogen, cycloalkyl, aryl or heteroaryl;
  Z is a single bond or —C(=O)—;
  $R^1$, $R^2$, $R^3$, $R^4$ and $R^5$ are independently hydrogen or alkyl said alkyl being optionally substituted with hydroxy;
  alk is an alkylene chain of one to six carbon atoms;
  X is —O—, —$NR^b$-(where $R^b$ is hydrogen or alkyl), $(CR^6R^7)_m$ [where $R^6$ and $R^7$ are independently in each occurrence hydrogen or alkyl, and m is an integer from 0 to 3],
  or —$S(O)_n$-(wherein n is an integer from 0 to 2);
or prodrugs, individual isomers, racemic and non-racemic mixtures of isomers, and pharmaceutically acceptable salts or solvates thereof.

In a second aspect, this invention provides a pharmaceutical composition comprising a therapeutically effective amount of a compound of Formula (I) or its pharmaceutically acceptable salt and a pharmaceutically acceptable excipient.

In a third aspect, this invention provides a method of treatment of a disease in a mammal treatable by administration of a CCR-3 receptor antagonist, comprising administration of a pharmaceutical composition comprising a therapeutically effective amount of a compound of Formula (I) or its pharmaceutically acceptable salt and a pharmaceutically acceptable excipient. The disease states include respiratory diseases such as asthma.

In a fourth aspect, this invention provides a process for preparing compounds of Formula (I).

DETAILED DESCRIPTION OF THE INVENTION

Definitions

Unless otherwise stated, the following terms used in the specification and claims have the meanings given below:

"Acyl" means a radical —C(O)R, where R is hydrogen, alkyl, cycloalkyl, cycloalkylalkyl, phenyl, or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R' is hydrogen or alkyl, and R is hydrogen, alkyl, cycloalkyl, cycloalkylalkyl, phenyl, or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethylcarbonylamino, benzoylamino, benzylcarbonylamino, and the like.

"Alkoxy" means a radical —OR where R is alkyl as defined herein e.g., methoxy, ethoxy, propoxy, butoxy and the like.

"Alkoxycarbonyl" means a radical —C(O)—R where R is alkoxy is as defined herein.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to four carbon atoms or a branched saturated divalent hydrocarbon radical of three to six carbon atoms, e.g., methylene, ethylene, 2,2-dimethylethylene, propylene, 2-methylpropylene, butylene, and the like.

"Alkylsulfonyl" means a radical —S(O)$_2$R where R is an alkyl, cycloalkyl, or cycloalkyl-alkyl group as defined herein, e.g., methylsulfonyl, ethylsulfonyl, propylsulfonyl, butylsulfonyl, cyclohexylsulfonyl, and the like.

"Alkylsulfinyl" means a radical —S(O)R where R is an alkyl, cycloalkyl, or cycloalkyl-alkyl group as defined herein e.g., methylsulfinyl, ethylsulfinyl, propylsulfinyl, butylsulfinyl, cyclohexylsulfinyl, and the like.

"Alkylthio" means a radical —SR where R is an alkyl as defined above e.g., methylthio, ethylthio, propylthio, butylthio, and the like.

"Aryl" means a monocyclic or bicyclic aromatic hydrocarbon radical which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, thio, methylenedioxy, and ethylenedioxy. Additionally, the term aryl also includes such rings having a heterocyclic, heteroaryl, or cycloalkyl ring fused thereto, with the understanding that the point of attachment of the aryl radical will be on an aromatic carbocyclic ring. More specifically the term aryl includes, but is not limited to, phenyl, chlorophenyl, fluorophenyl, methoxyphenyl, 1-naphthyl, 2-naphthyl, benzodioxolyl, and derivatives thereof.

"Arylalkyl" refers to an alkyl radical as defined herein in which one of the hydrogen atoms of the alkyl group is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl, and the like.

"Arylalkyloxy" means a radical —O—R where R is arylalkyl as defined herein.

"Aryloxy" means a radical —O—R where R is an aryl group as defined herein.

"Cycloalkyl" refers to a saturated monovalent cyclic hydrocarbon radical of three to seven ring carbons e.g., cyclopropyl, cyclobutyl, cyclohexyl, 4-methylcyclohexyl, and the like.

"Cycloalkyl-alkyl" means a radical —R$^a$R$^b$ where R$^a$ is an alkylene group and R$^b$ is cycloalkyl group as defined herein, e.g., cyclohexylmethyl, and the like.

"Dialkylamino" means a radical —NRR' where R and R' independently represent alkyl, cycloalkyl, or cycloalkylalkyl groups as defined herein. Representative examples include, but are not limited to, dimethylamino, methylethylamino, di(1-methylethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, thio, methylenedioxy, or ethylenedioxy. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl, or benzothienyl and derivatives thereof.

"Heteroarylalkyl means an alkyl radical as defined herein in which one of the hydrogen atoms of the alkyl group is replaced with a heteroaryl group.

"Heterocyclyl" means a saturated or unsaturated non-aromatic cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino, dialkylamino, aralkyl, —(X)$_n$—C(O)R (where, X is O or NR', n is 0 or 1, R is hydrogen, alkyl, haloalkyl, hydroxy, alkoxy, amino, monoalkylamino, dialkylamino, or optionally substituted phenyl, and R' is H or alkyl), -alkylene-C(O)R (where R is hydrogen, alkyl, haloalkyl, hydroxy, alkoxy, amino, monoalkylamino, dialkylamino, or optionally substituted phenyl), or —S(O)$_n$R$^d$ (where n is an integer from 0 to 2, and when n is 0, R$^d$ is hydrogen, haloalkyl, alkyl, cycloalkyl, or cycloalkylalkyl, and when n is 1 or 2, R$^d$ is alkyl, haloalkyl, hydroxyalkyl, cycloalkyl, cycloalkylalkyl, amino, acylamino, monoalkylamino, or dialkylamino). More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, and the derivatives thereof.

"Heterocyclylalkyl" means a radical —$R^aR^b$ where $R^a$ is an alkylene group and $R^b$ is a heterocyclyl group as defined above with the understanding that $R^b$ is attached to $R^a$ via a carbon atom of the heterocyclyl ring, e.g., tetrahydropyran-2-ylmethyl, 2- or 3-piperidinylmethyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:
(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or
(2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1–92, Elesevier, New York-Oxford (1985), and the like.

"Protecting group" refers to a grouping of atoms that when attached to a reactive group in a molecule masks, reduces, or prevents that reactivity. Examples of protecting groups can be found in T. W. Green and P. G. Futs, *Protective Groups in Organic Chemistry*, (Wiley, $2^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxy-carbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl and trityl ethers as well as alkyl ethers, tetrahydropyranyl ethers, trialkylsilyl ethers, and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity, and the age, weight, etc. of the mammal to be treated.

Representative compounds of this invention are as follows:
I. Representative compounds of Formula (I) where $R^1$–$R^5$ are hydrogen and Z is a single bond:

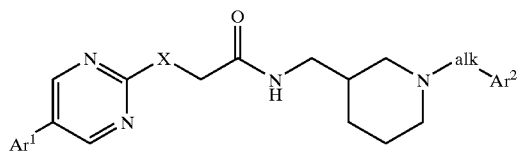
| Cpd # | Structure | CCR-3 IC50 μM | NAME |
|---|---|---|---|
| 1 | [RAC] | 0.025 | 2-[5-(3,4-dimethoxy-phenyl)-pyrimidin-2-ylsulfanyl]-N-[1-(1H-indol-6-ylmethyl)-piperidin-3-(ylmethyl]-acetamide |
| 2 | [RAC] | 0.029 | N-[1-(3,4-dichloro-benzyl)-piperidin-3-ylmethyl]-2-[5-(3,4-dimethoxy-phenyl)-pyrimidin-2-ylsulfanyl]-acetamide |
| 3 | 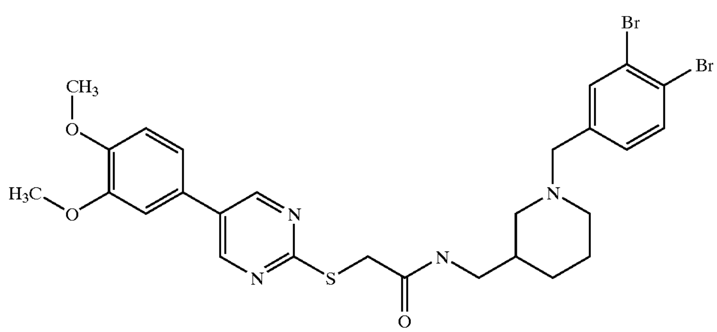 | | N-[1-(3,4-dibromo-benzyl)-piperidin-3-ylmethyl]-2-[5-(3,4-dimethoxy-phenyl)-pyrimidin-2-ylsulfanyl]-acetamide |

| | | | |
|---|---|---|---|
| 4 | 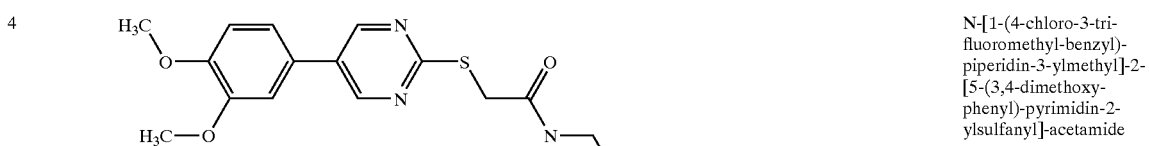 | | N-[1-(4-chloro-3-tri-fluoromethyl-benzyl)-piperidin-3-ylmethyl]-2-[5-(3,4-dimethoxy-phenyl)-pyrimidin-2-ylsulfanyl]-acetamide |
| 5 |  | | N-[1-(3,4-dichloro-benzyl)-piperidin-3-ylmethyl]-2-[5-(3,4-dimethoxy-phenyl)-pyrimidin-2-ylsulfanyl]-acetamide |
| 6 | 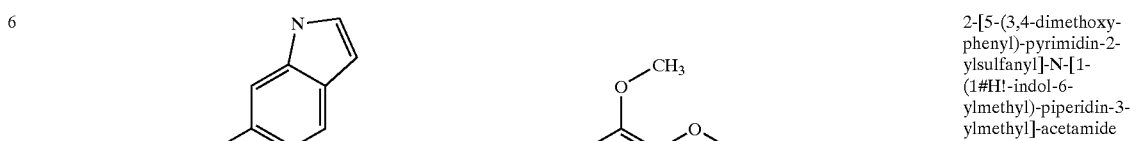 | | 2-[5-(3,4-dimethoxy-phenyl)-pyrimidin-2-ylsulfanyl]-N-[1-(1#H!-indol-6-ylmethyl)-piperidin-3-ylmethyl]-acetamide |
| 7 |  | | N-[1-(2,3-dichloro-benzyl)-piperidin-3-ylmethyl]-2-[5-(3,4-dimethoxy-phenyl)-pyrimidin-2-ylsulfanyl]-acetamide-acetamide |
| 8 | 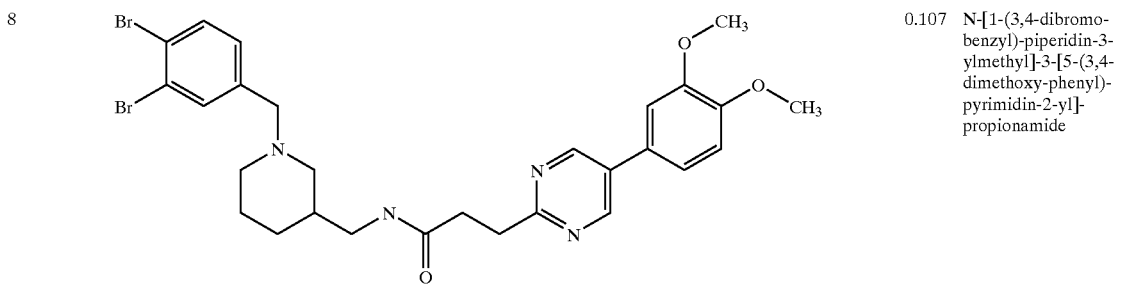 | 0.107 | N-[1-(3,4-dibromo-benzyl)-piperidin-3-ylmethyl]-3-[5-(3,4-dimethoxy-phenyl)-pyrimidin-2-yl]-propionamide |

| | | | |
|---|---|---|---|
| 9 | 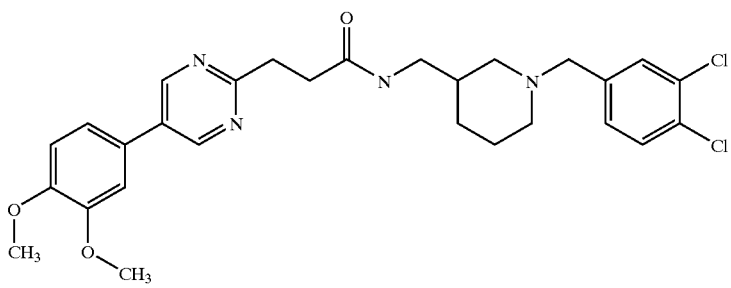 | 0.152 | N-[1-(3,4-dichloro-benzyl)-piperidin-3-ylmethyl]-3-[5-(3,4-dimethoxy-phenyl)-pyrimidin-2-yl]-propionamide |
| 10 | 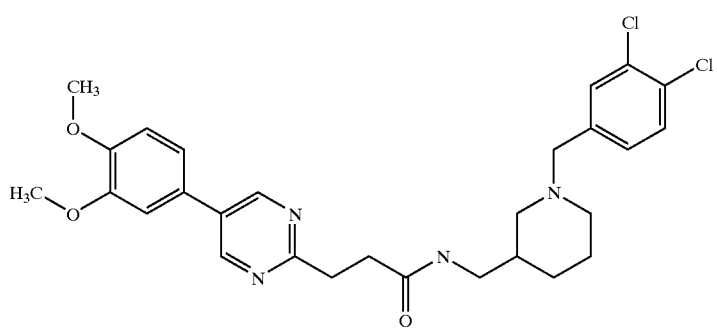 | 0.164 | N-[1-(3,4-dichloro-benzyl)-piperidin-3-ylmethyl]-3-[5-(3,4-dimethoxy-phenyl)-pyrimidin-2-yl]-propionamide |
| 11 | 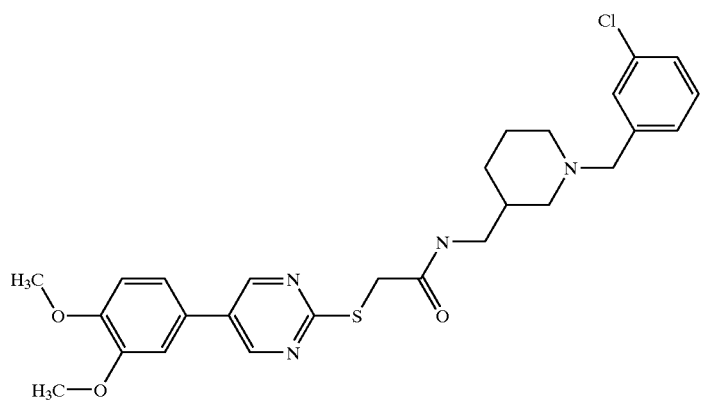 | | N-[1-(3-chloro-benzyl)-piperidin-3-ylmethyl]-2-[5-(3,4-dimethoxy-phenyl)-pyrimidin-2-ylsulfanyl]-acetamide |
| 12 | 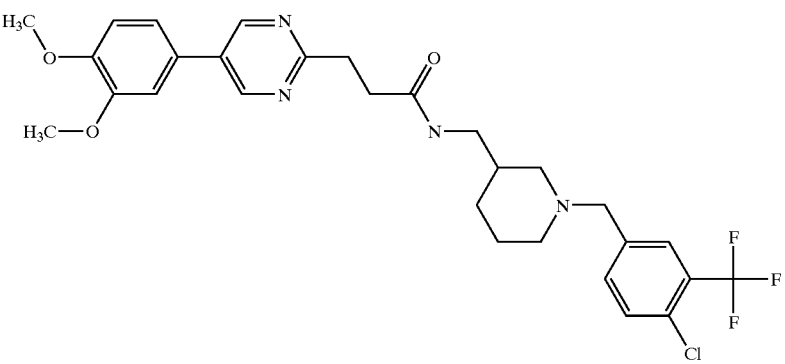 | | N-[1-(4-chloro-3-trifluoromethyl-benzyl)-piperidin-3-ylmethyl]-3-[5-(3,4-dimethoxy-phenyl)-pyrimidin-2-yl]-propionamide |

| | | | |
|---|---|---|---|
| 13 | 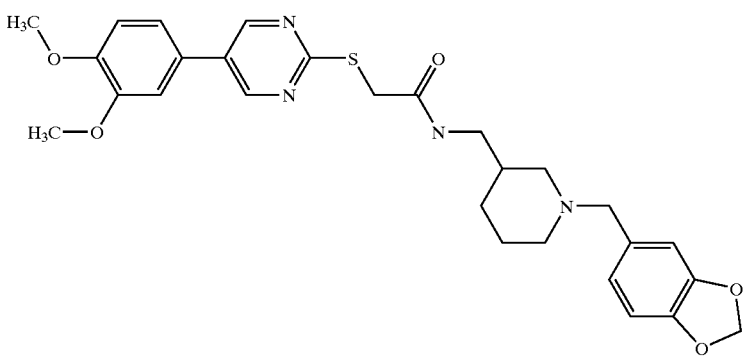 | 0.205 | N-(1-benzo[1,3]-dioxol-5-ylmethyl-piperidin-3-ylmethyl]-2-[5-(3,4-dimethoxy-phenyl)-pyrimidin-2-ylsulfanyl]-acetamide |
| 14 | 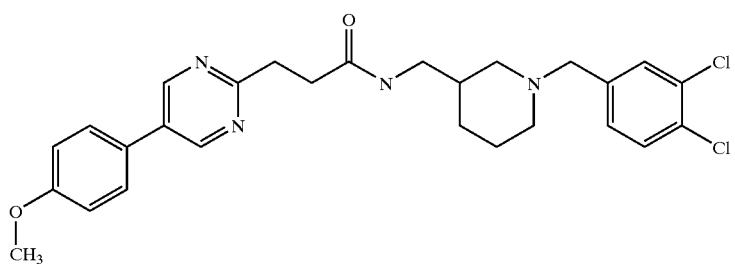 [RAC] | | N-[1-(3,4-dichloro-benzyl)-piperidin-3-ylmethyl]-3-[5-(4-methoxy-phenyl)-pyrimidin-2-yl]-propionamide |
| 15 | 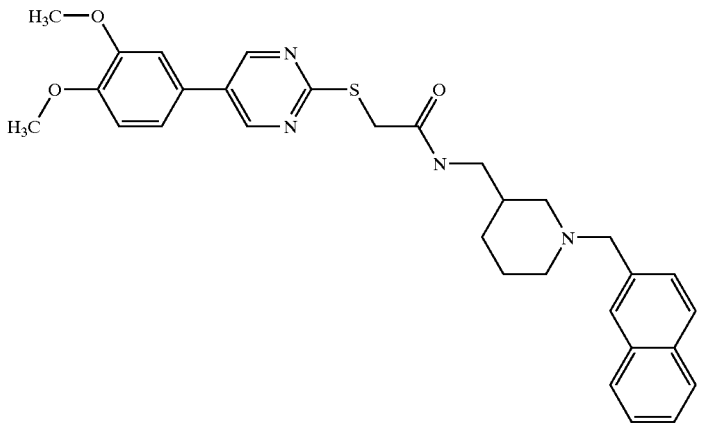 | 0.263 | 2-[5-(3,4-dimethoxy-phenyl)-pyrimidin-2-ylsulfanyl]-N-(1-naphthalen-2-yl-methyl-piperidin-3-ylmethyl)-acetamide |
| 16 | 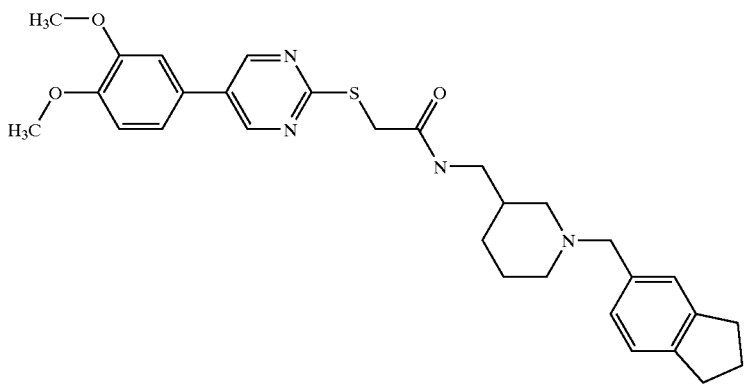 | 0.276 | 2-[5-(3,4-dimethoxy-phenyl)-pyrimidin-2-ylsulfanyl]-N-(1-indan-5-ylmethyl-piperidin-3-ylmethyl)-acetamide |

| | | |
|---|---|---|
| 17 | 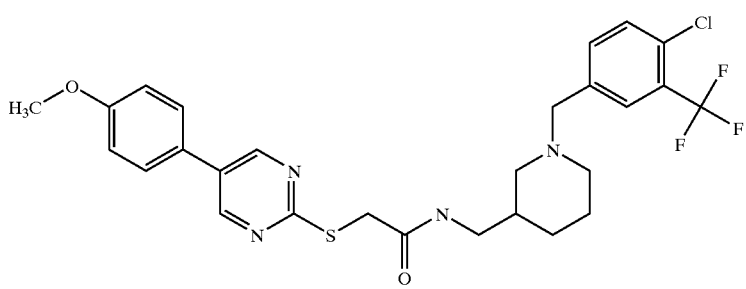 | N-[1-(4-chloro-3-trifluoromethyl-benzyl)-piperidin-3-ylmethyl]-2-[5-(4-methoxy-phenyl)-pyrimidin-2-ylsulfanyl]-acetamide |
| 18 | 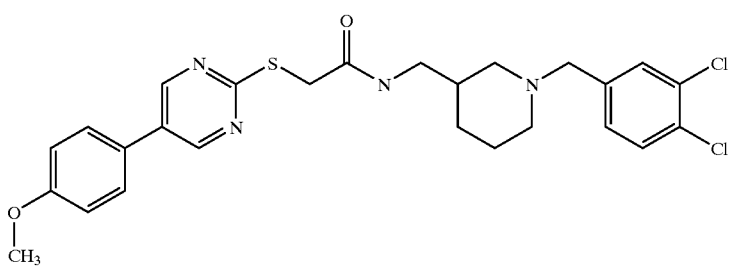 | N-[1-(3,4-dichloro-benzyl)-piperidin-3-ylmethyl]-2-[5-(4-methoxy-phenyl)-pyrimidin-2-yl-sulfanyl]-acetamide |
| 19 | 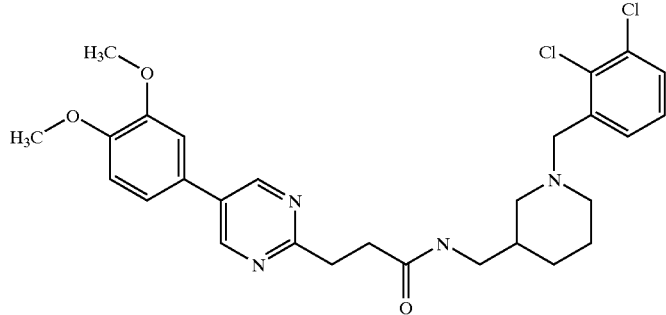 | N-[1-(2,3-dichloro-benzyl)-piperidin-3-ylmethyl]-3-[5-(3,4-dimethoxy-phenyl)-pyrimidin-2-yl]-propionamide |
| 20 | 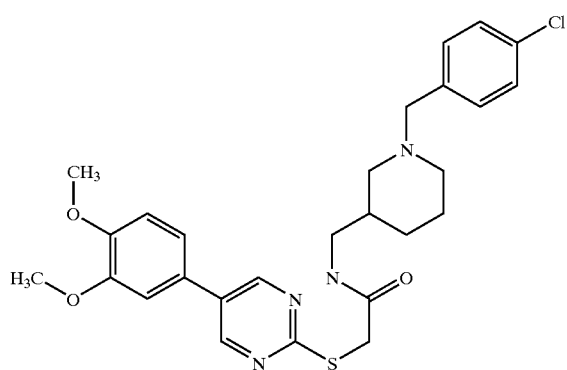 | N-[1-(4-chloro-benzyl)-pipendin-3-ylmethyl]-2-[5-(3,4-dimethoxy-phenyl)-pyrimidin-2-yl-sulfanyl]-acetamide |
| 21 | 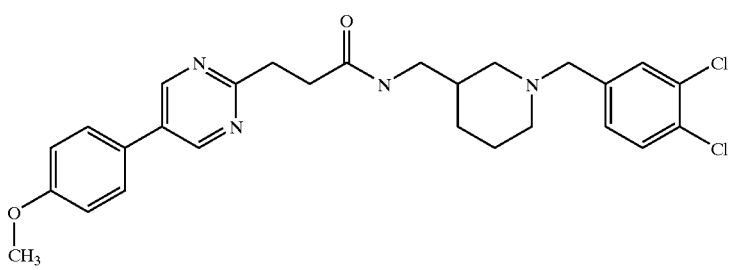 | N-[1-(3,4-dichloro-benzyl)-piperidin-3-ylmethyl]-3-[5-(4-methoxy-phenyl)-pyrimidin-2-yl]-propionamide |

| | | | |
|---|---|---|---|
| 22 | 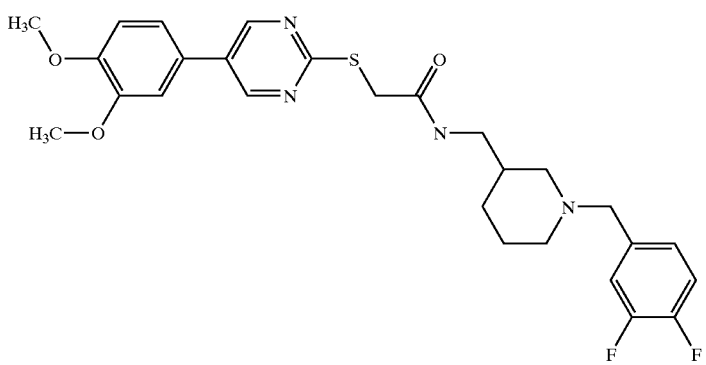 | | N-[1-(3,4-difluoro-benzyl)-piperidin-3-ylmethyl]-2-[5-(3,4-dimethoxy-phenyl)-pyrimidin-2-ylsulfanyl]-acetamide |
| 23 | 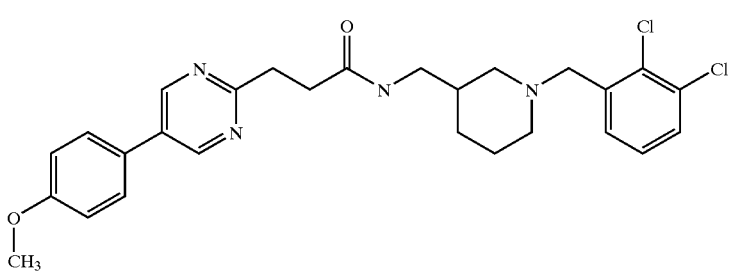 | 0.403 | N-[1-(2,3-dichloro-benzyl)-piperidin-3-ylmethyl]-3-[5-(4-methoxy-phenyl)-pyrimidin-2-yl]-propionamide |
| 24 | 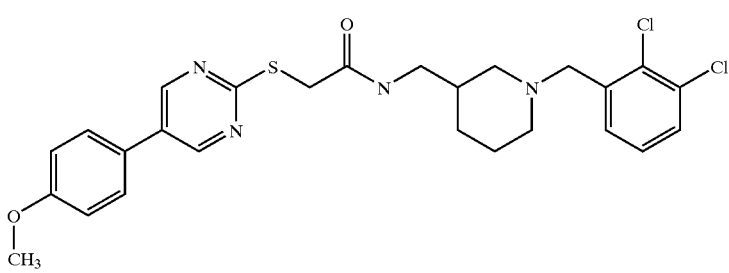 | | N-[1-(2,3-dichloro-benzyl)-piperidin-3-ylmethyl]-2-[5-(4-methoxy-phenyl)-pyrimidin-2-ylsulfanyl]-acetamide |
| 25 | 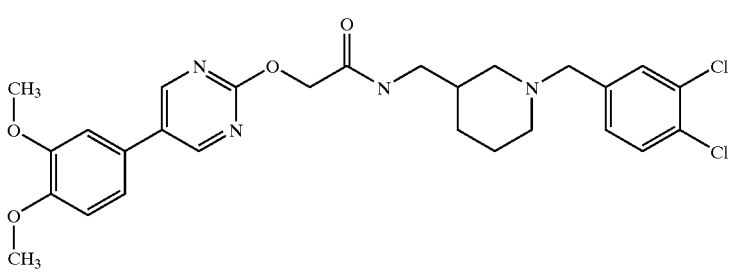 | | N-[1-(3,4-dichloro-benzyl)-piperidin-3-ylmethyl]-2-[5-(3,4-dimethoxy-phenyl)-pyrimidin-2-yloxy]-acetamide |
| 26 | 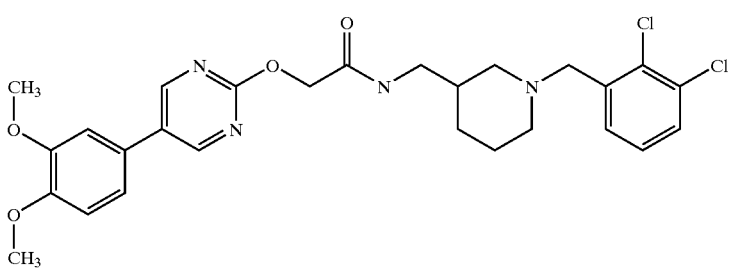 | 0.507 | N-[1-(2,3-dichloro-benzyl)-piperidin-3-ylmethyl]-2-[5-(3,4-dimethoxy-phenyl)-pyrimidin-2-yloxy]-acetamide |

| | | |
|---|---|---|
| 27 | 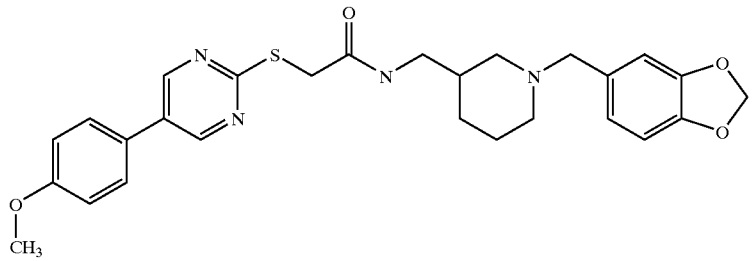 | N-(1-benzo[1,3]-dioxol-5-ylmethyl-piperidin-3-ylmethyl)-2-[5-(4-methoxy-phenyl)-pyrimidin-2-ylsulfanyl]-acetamide |
| 28 | 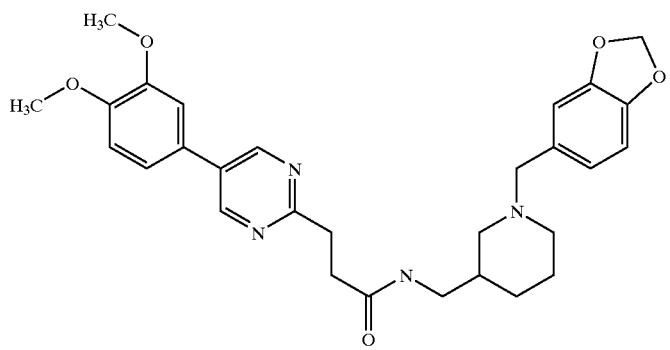 | N-(1-benzo[1,3]-dioxol-5-ylmethyl-piperidin-3-ylmethyl)-3-[5-(3,4-dimethoxy-phenyl)-pyrimidin-2-yl]-propionamide |
| 29 | 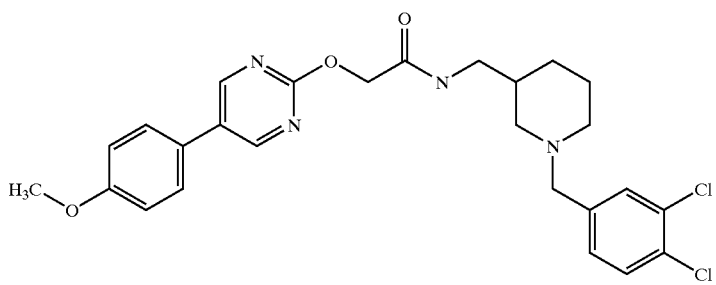 | N-[1-(3,4-dichloro-benzyl)-piperidin-3-ylmethyl]-2-[5-(4-methoxy-phenyl)-pyrimidin-2-yloxy]-acetamide |
| 30 | 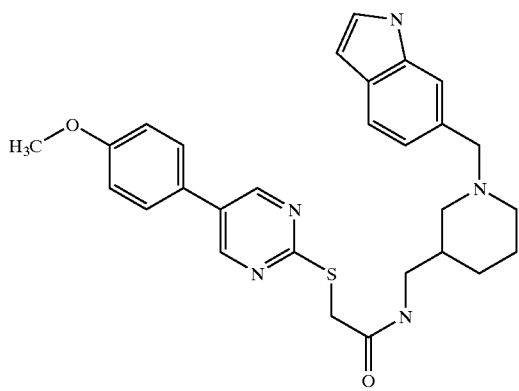 0.731 | N-[1H-indol-6-ylmethyl)-piperidin-3-ylmethyl]-2-[5-(4-methoxy-phenyl)-pyrimidin-2-yl-sulfanyl]-acetamide |
| 31 | 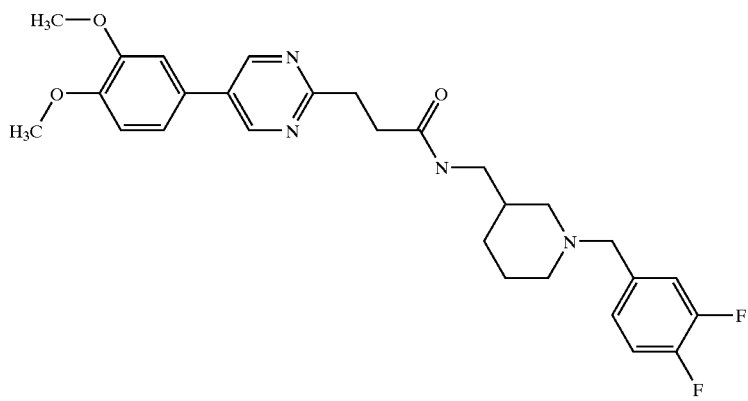 | N-[1-(3,4-difluoro-benzyl)-piperidin-3-ylmethyl]-3-[5-(3,4-dimethoxy-phenyl)-pyrimidin-2-yl]-propionamide |

| | | | |
|---|---|---|---|
| 32 | 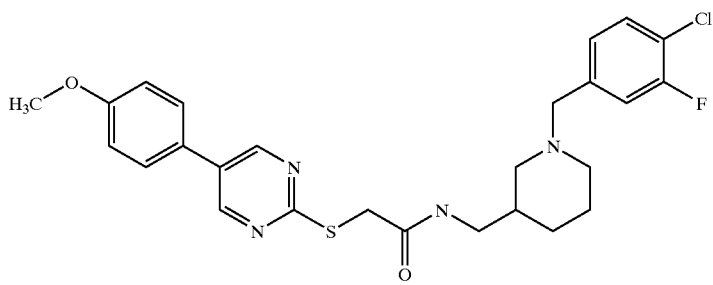 | | N-[1-(4-chloro-3-fluoro-benzyl)-piperidin-3-ylmethyl]-2-[5-(4-methoxy-phenyl)-pyrimidin-2-ylsulfanyl]-acetamide |
| 33 | 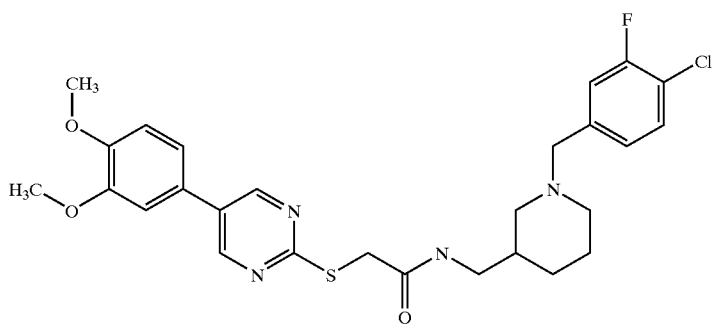 | 0.973 | N-[1-(4-chloro-3-fluoro-benzyl)-piperidin-3-ylmethyl]-2-[5-(3,4-dimethoxy-phenyl)-pyrimidin-2-ylsulfanyl]-acetamide |
| 34 | 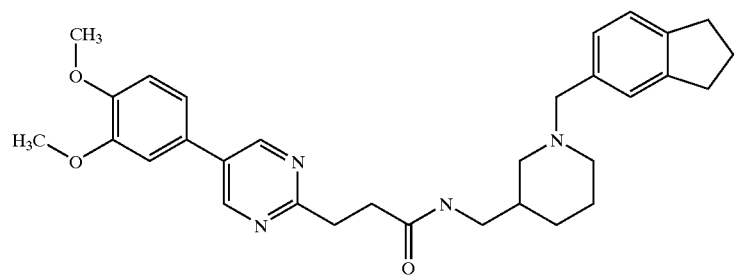 | 0.994 | 3-[5-(3,4-dimethoxy-phenyl)-pyrimidin-2-yl]-N-(1-indan-5-yl-methyl-piperidin-3-ylmethyl)-propion-amide |
| 35 | 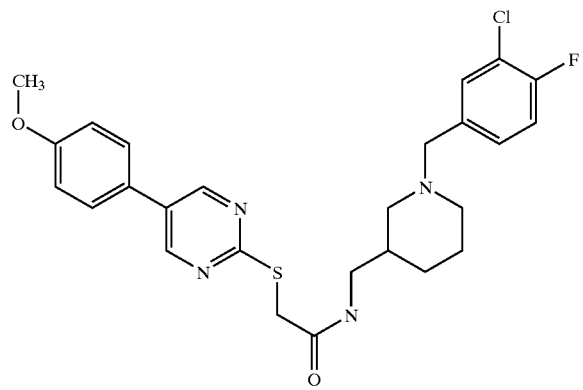 | | N-[1-(3-chloro-4-fluoro-benzyl)-piperidin-3-ylmethyl]-2-[5-(4-methoxy-phenyl)-pyrimidin-2-ylsulfanyl]-acetamide |
| 36 | 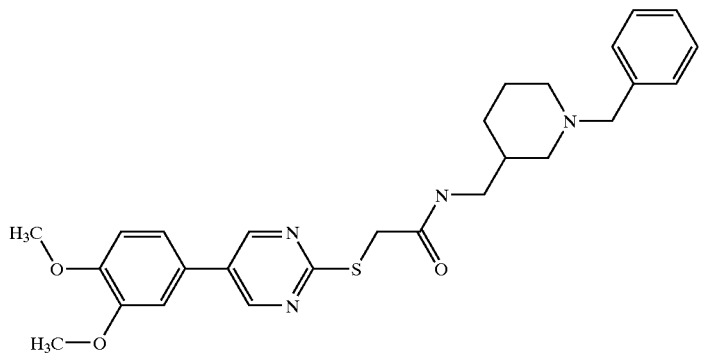 | 1.06 | N-(1-benzyl-piperidin-3-ylmethyl)-2-[5-(3,4-dimethoxy-phenyl)-pyrimidin-2-ylsulfanyl]-acetamide |

| | | | |
|---|---|---|---|
| 37 | 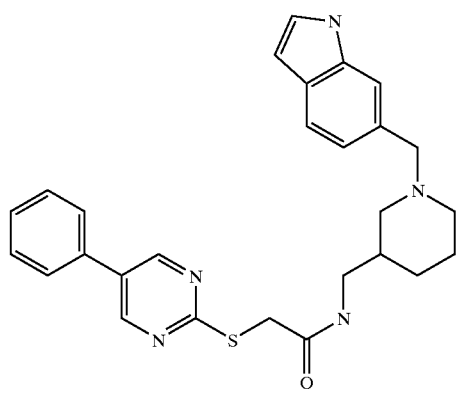 | | N-[1-(1H-indol-6-ylmethyl)-piperidin-3-ylmethyl]-2-(5-phenyl-pyrimidin-2-ylsulfanyl)-acetamide |
| 38 | 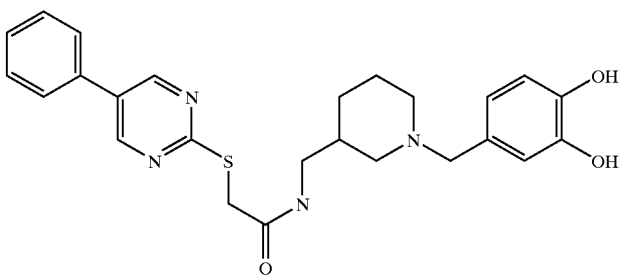 | 1.35 | N-[1-(3,4-dihydroxy-benzyl)-piperidin-3-ylmethyl]-2-(5-phenyl-pyrimidin-2-ylsulfanyl)-acetamide |
| 39 | 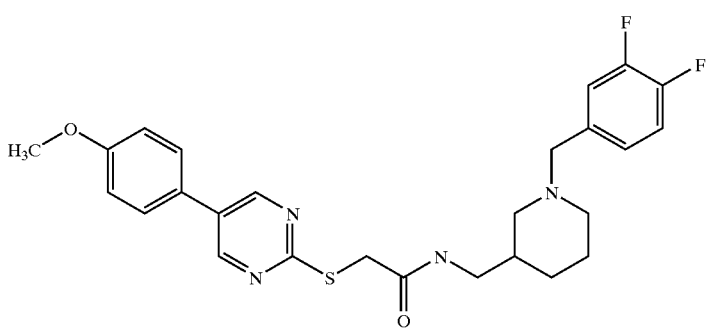 | 1.37 | N-[1-(3,4-difluoro-benzyl)-piperidin-3-ylmethyl]-2-[5-(4-methoxy-phenyl)-pyrimidin-2-ylsulfanyl]-acetamide |
| 40 | 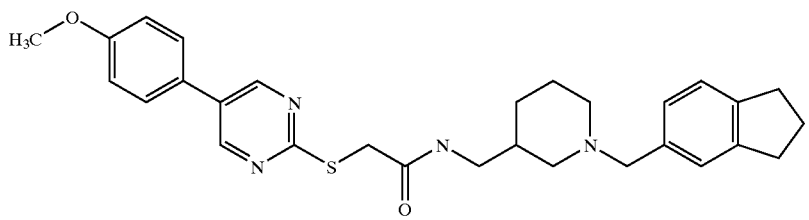 | 1.39 | N-(1-indan-5-ylmethyl-piperidin-3-ylmethyl)-2-[5-(4-methoxy-phenyl)-(pyrimidin-2-ylsulfanyl]-acetamide |
| 41 | 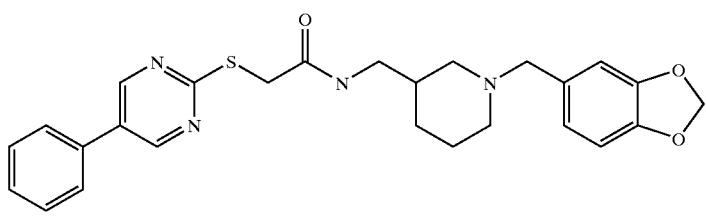 | 1.56 | N-(1-benzo[1,3]-dioxol-5-ylmethyl-piperidin-3-ylmethyl)-2-(5-phenyl-pyrimidin-2-ylsulfanyl)-acetamide |
| 42 | 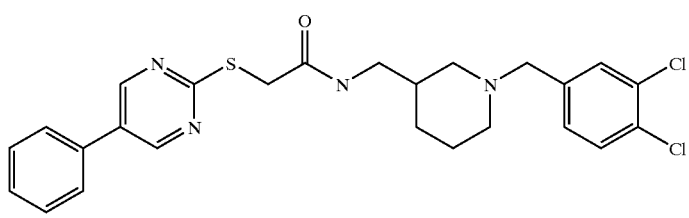 | 1.56 | N-[1-(3,4-dichloro-benzyl)-piperidin-3-ylmethyl]-2-(5-phenyl-pyrimidin-2-ylsulfanyl)-acetamide |

| | | | |
|---|---|---|---|
| 43 | 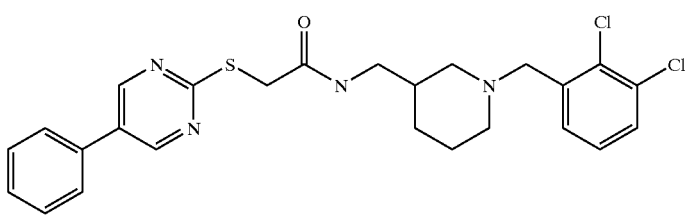 | | N-[1-(2,3-dichloro-benzyl)-piperidin-3-ylmethyl]-2-(5-phenyl-pyrimidin-2-ylsulfanyl)-acetamide |
| 44 | 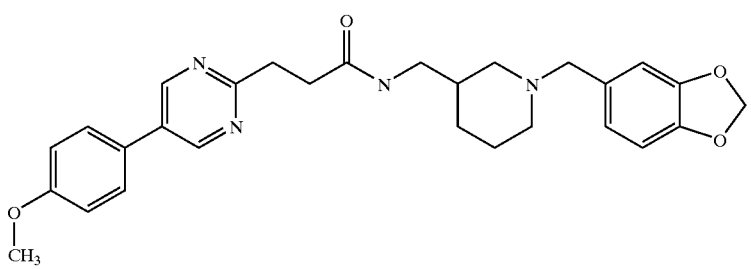 | 2.08 | N-(1-benzo[1,3]-dioxol-5-ylmethyl-piperidin-3-ylmethyl)-3-[5-(4-methoxy-phenyl)-pyrimidin-2-yl]-propionamide |
| 45 | 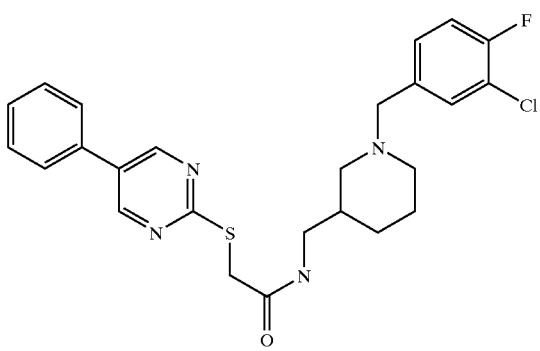 | | N-[1-(3-chloro-4-fluoro-benzyl)-piperidin-3-ylmethyl]-2-(5-phenyl-pyrimidin-2-ylsulfanyl)-acetamide |
| 46 | 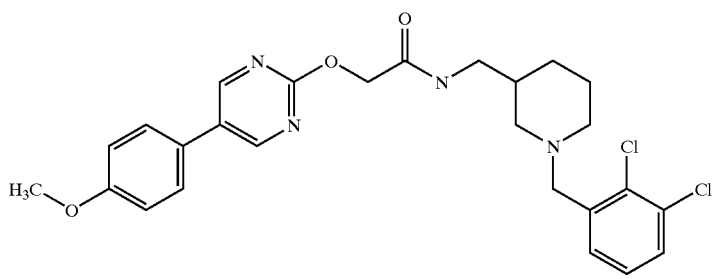 | 2.11 | N-[1-(2,3-dichloro-benzyl)-piperidin-3-ylmethyl]-2-[5-(4-methoxy-phenyl)-pyrimidin-2-yloxy]-acetamide |
| 47 | 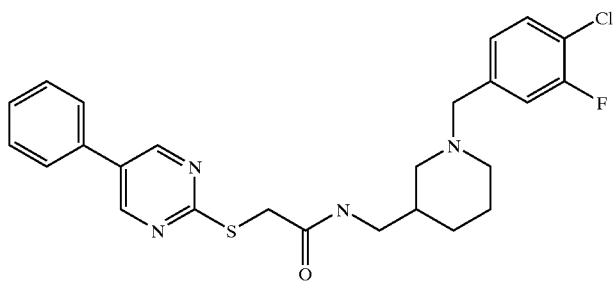 | | N-[1-(4-chloro-3-fluoro-benzyl)-piperidin-3-ylmethyl]-2-(5-phenyl-pyrimidin-2-ylsulfanyl)-acetamide |
| 48 | 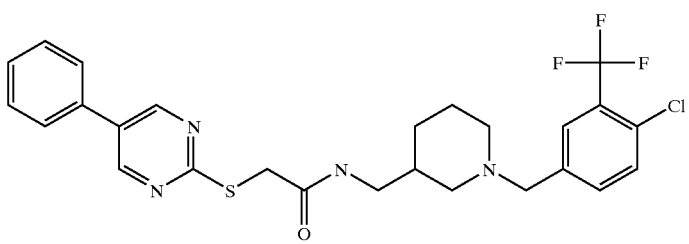 | 2.41 | N-[1-(4-chloro-3-trifluoromethyl-benzyl)-piperidin-3-ylmethyl]-2-(5-phenyl-pyrimidin-2-yl-sulfanyl)-acetamide |

| | | | |
|---|---|---|---|
| 49 | 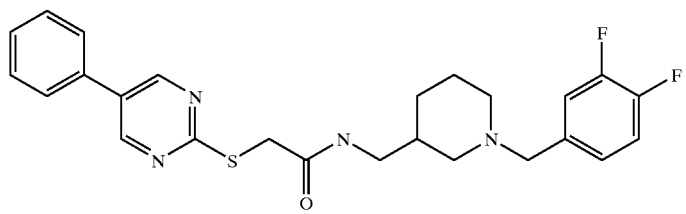 | 2.81 | N-[1-(3,4-difluoro-benzyl)-piperidin-3-ylmethyl]-2-(5-phenyl-pyrimidin-2-ylsulfanyl)-acetamide |
| 50 | 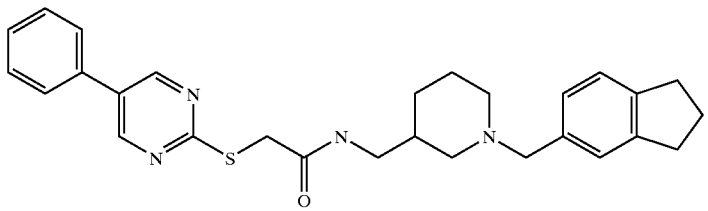 | | N-(1-indan-5-ylmethyl-piperidin-3-ylmethyl)-2-(5-phenyl-pyrimidin-2-ylsulfanyl)-acetamide |
| 51 | 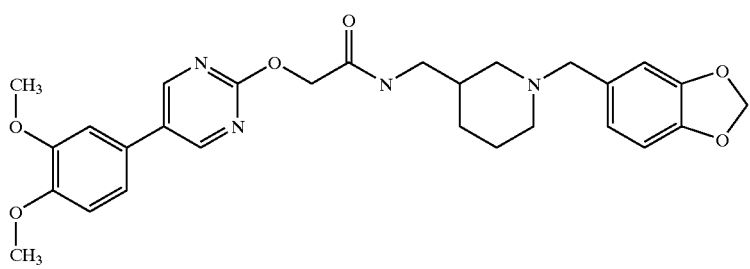 | 4.64 | N-(1-benzo[1,3]-dioxol-5-ylmethyl-piperidin-3-ylmethyl)-2-[5-(3,4-dimethoxy-phenyl)-pyrimidin-2-yloxy]-acetamide |
| 52 | 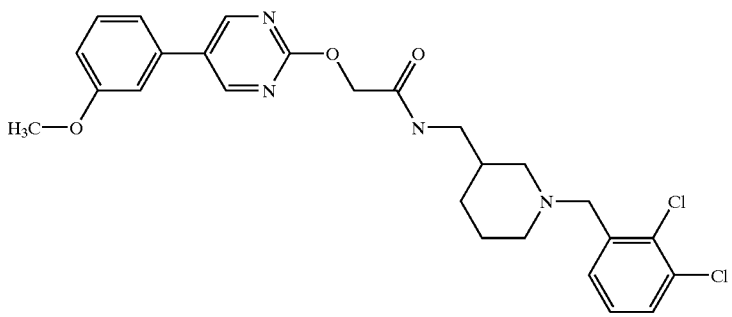 | 5.74 | N-[1-(2,3-dichloro-benzyl)-piperidin-3-ylmethyl]-2-[5-(3-methoxy-phenyl)-pyrimidin-2-yloxy]-acetamide |
| 53 | 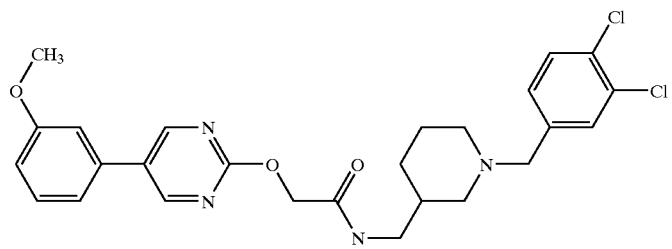 | | N-[1-(3,4-dichloro-benzyl)-piperidin-3-ylmethyl]-2-[5-(3-methoxy-phenyl)-pyrimidin-2-yloxy]-acetamide |
| 54 | 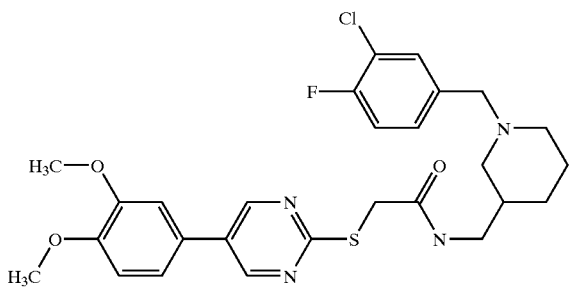 | | N-[1-(3-chloro-4-fluoro-benzyl)-piperidin-3-ylmethyl]-2-[5-(3,4-dimethoxy-phenyl)-pyrimidin-2-ylsulfanyl]-acetamide |

| | | | |
|---|---|---|---|
| 55 | 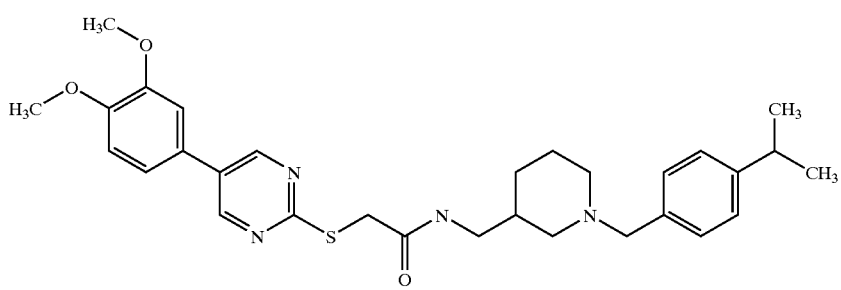 | | 2-[5-(3,4-dimethoxy-phenyl)-pyrimidin-2-ylsulfanyl]-N-[1-(4-isopropyl-benzyl)-piperidin-3-ylmethyl]-acetamide |
| 56 | 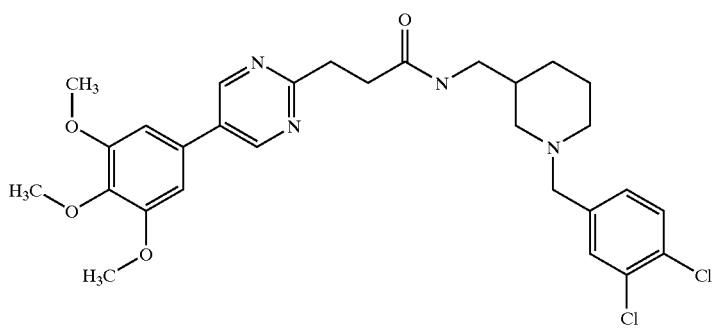 | | N-[1-(3,4-dichloro-benzyl)-piperidin-3-ylmethyl]-3-[5-(3,4,5-trimethoxy-phenyl)-pyrimidin-2-yl]-propionamide |
| 57 | 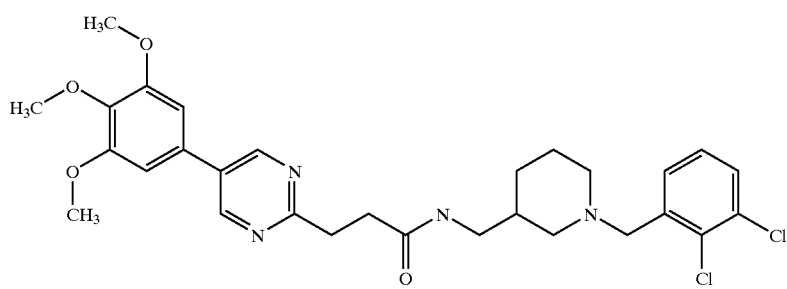 | 12 | N-[1-(2,3-dichloro-benzyl)-piperidin-3-ylmethyl]-3-[5-(3,4,5-trimethoxy-phenyl)-pyrimidin-2-yl]-propionamide |
| 58 | 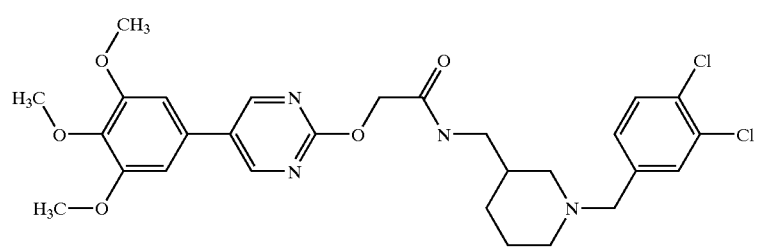 | 21 | N-[1-(3,4-dichloro-benzyl)-piperidin-3-ylmethyl]-2-[5-(3,4,5-trimethoxy-phenyl)-pyrimidin-2-yloxy]-acetamide |
| 59 | 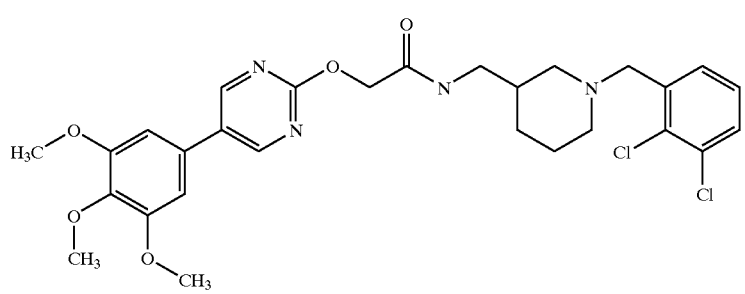 | | N-[1-(2,3-dichloro-benzyl)-piperidin-3-ylmethyl]-2-[5-(3,4,5-trimethoxy-phenyl)-pyrimidin-2-yloxy]-acetamide |

| | | | |
|---|---|---|---|
| 60 | 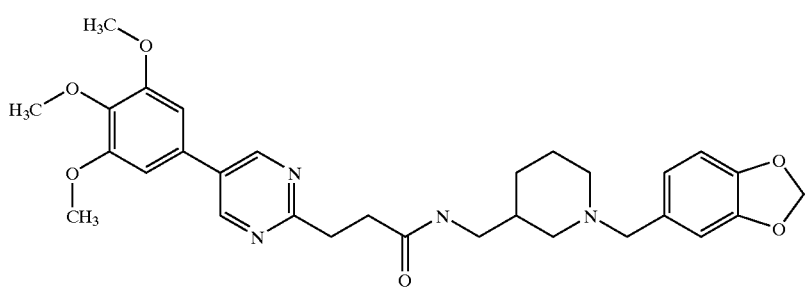 | | N-(1-benzo[1,3]-dioxol-5-ylmethyl-piperidin-3-ylmethyl)-3-[5-(3,4,5-trimethoxy-phenyl)-pyrimidin-2-yl]-propionamide |
| 61 | 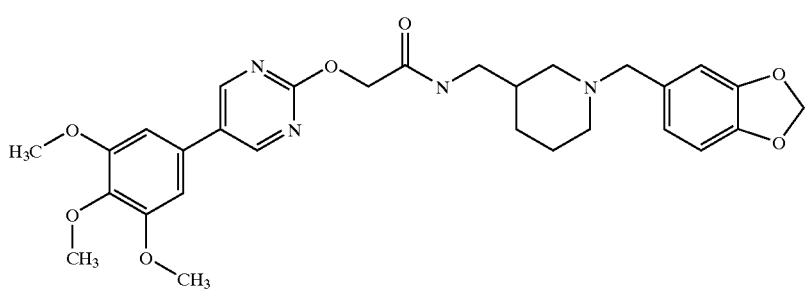 | | N-(1-benzo[1,3]-dioxol-5-ylmethyl-trimethoxy-phenyl)-pyrimidin-2-yloxy]-acetamide |
| 62 | 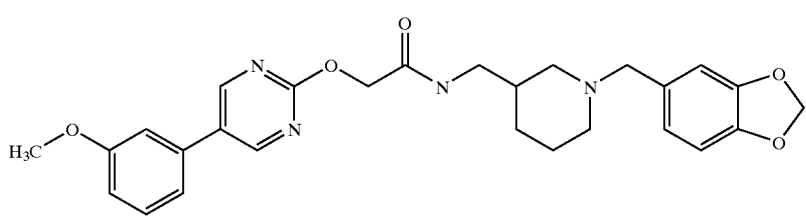 | 128 | N-(1-benzo[1,3]-dioxol-5-ylmethyl-piperidin-3-ylmethyl)-2-[5-(3-methoxy-phenyl)-pyrimidin-2-yloxy]-acetamide |
| 63 | 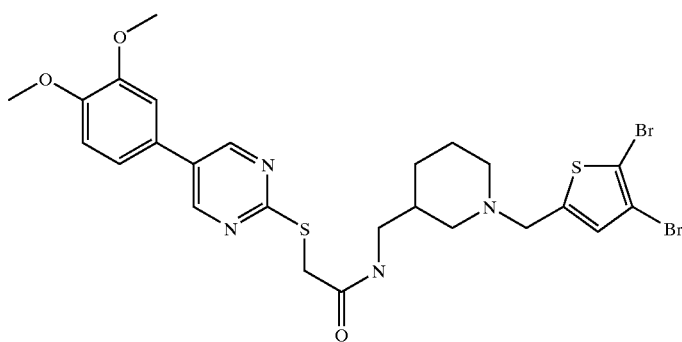 | 0.066 | N-[1-(4,5-dibromo-thiophen-2-ylmethyl)-piperidin-3-ylmethyl]-2-[5-(3,4-dimethoxy-phenyl)-pyrimidin-2-ylsulfanyl]-acetamide |
| 64 | 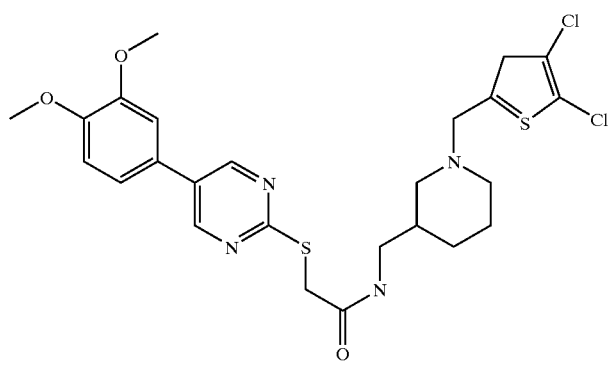 | 0.081 | N-[1-(4,5-dichloro-thiophen-2-ylmethyl)-piperidin-3-ylmethyl]-2-[5-(3,4-dimethoxy-phenyl)-pyrimidin-2-ylsulfanyl]-acetamide |

| | | |
|---|---|---|
| 65 | 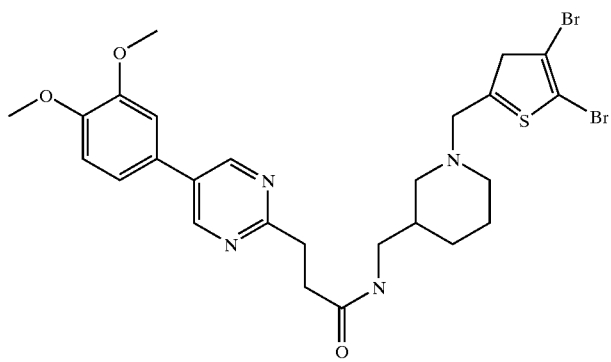 | 0.994 N-[1-(4,5-dichloro-thiophen-2-ylmethyl)-piperidin-3-ylmethyl]-3-[5-(3,4-dimethoxy-phenyl)-pyrimidin-2-yl]-propionamide |
| 66 | 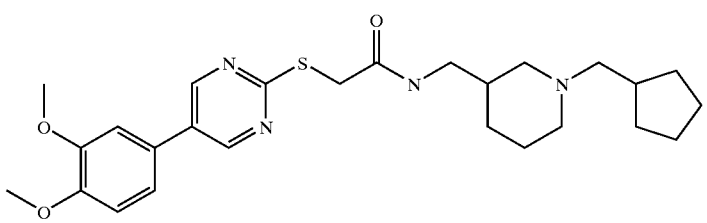 | N-(1-Cyclopentyl-methyl-piperidin-3-ylmethyl)-2-[5-(3,4-dimethoxyphenyl)-pyrimidin-2-yl-sulfanyl]-acetamide |
| 67 | 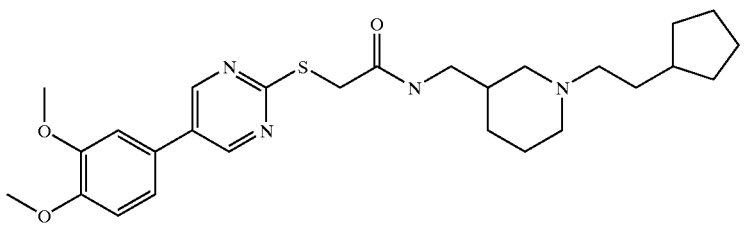 | N-[1-(2-Cyclopentyl-ethyl)-piperidin-3-ylmethyl]-2-[5-(3,4-dimethoxy-phenyl)-pyrimidin-2-yl-sulfanyl]-acetamide |
| 68 | 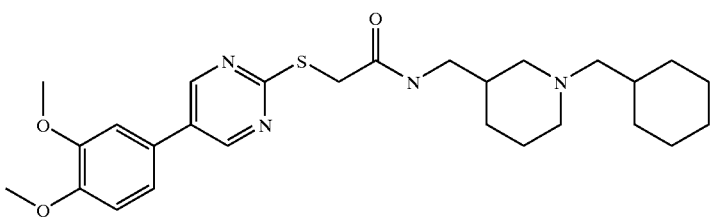 | N-(1-Cyclohexyl-methyl)-piperidin-3-ylmethyl)-2[5-(3,4-dimethoxyphenyl)-pyrimidin-2-yl-sulfanyl]-acetamide |
| 69 | 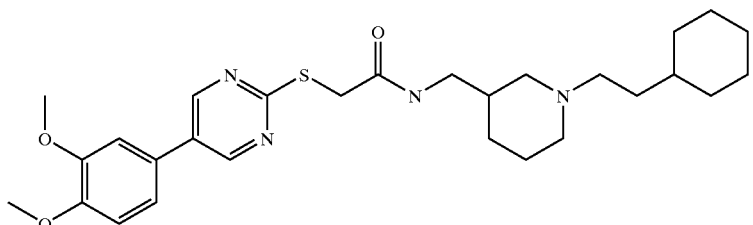 | N-[1-(2-Cyclohexyl-ethyl)-piperidin-3-ylmethyl]-2-[5-(3,4-dimethoxy-phenyl)-pyrimidin-2-yl-sulfanyl]-acetamide |

Compound 70. A compound of the invention where Z is —C(=O)— is: (±)-N-{1-[3-(4-Chlorophenyl)-propionyl]-piperidin-3-ylmethyl}-2-[5-(3,4-dimethoxy-phenyl)-pyrimidin-2-ylsulfanyl]-acetamide having an IC50 of 1.92 µM.

PREFERRED EMBODIMENTS

While the broadest definition of this invention is set forth in the Summary of the Invention, certain compounds of Formula (I) are preferred.

(A) A preferred group of compounds is that where $R^1$–$R^5$ are hydrogen.
(B) Another preferred group of compounds is that where $R^1$–$R^5$ are hydrogen and Z is a single bond.
(C) Another group of preferred compounds is that where $Ar^2$ is aryl or heteroaryl and a preferred subgroup within this group is that where $R^1$–$R^5$ are hydrogen and Z is a single bond and -alk- is —$CH_2$—.
(D) A preferred group of compounds of Formula (I) is represented by Formula (Ia):

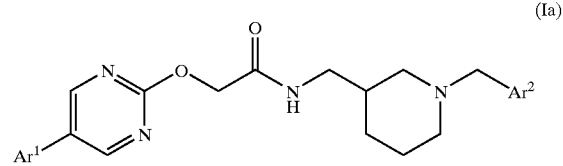

(Ia)

wherein:
$Ar^1$ is aryl; and

Ar² is aryl or heteroaryl.

(E) Another preferred group of compounds of Formula (I) is represented by Formula (Ib):

(Ib)

wherein:
Ar¹ is aryl;
Ar² is aryl or heteroaryl; and
$R^b$ is hydrogen or alkyl.

(F) Another preferred group of compounds of Formula (I) is represented by Formula (Ic):

(Ic)

wherein:
Ar¹ is aryl;
Ar² is aryl or heteroaryl;
$R^6$ and $R^7$ are independently in each occurrence hydrogen or alkyl; and
n is 0 to 3.

(G) Another preferred group of compounds of Formula (I) is represented by Formula (Id):

(Id)

wherein:
Ar¹ is aryl;
Ar² is aryl or heteroaryl;
wherein n is 0 to 2;
or prodrugs, individual isomers, racemic and non-racemic mixtures of isomers, and pharmaceutically acceptable salts or solvates thereof.

(H) Another preferred group of compounds is that where Ar² is aryl, particularly dihaloaryl, most particularly 3,4-dichlorophenyl and 2,3-dichlorophenyl.

(I) Another preferred group is where Z is a single bond and -alk- is —CH—₂—

GENERAL SYNTHETIC SCHEME

The compounds of the present invention can be prepared in a number of ways known to one skilled in the art. Preferred methods include, but are not limited to, the general synthetic procedures described below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA), Maybridge (Dist: Ryan Scientific, P.O. Box 6496, Columbia, S.C. 92960), Bionet Research Ltd., (Cornwall PL32 9QZ, UK), Menai Organics Ltd., (Gwynedd, N. Wales, UK), Butt Park Ltd., (Dist. Interchim, Montlucon Cedex, France), or are prepared by methods known to those skilled in the art following procedures set forth in references such as *Fieser and Fieser's Reagents for Organic Synthesis*, Volumes 1–17 (John Wiley and Sons, 1991), *Rodd's Chemistry of Carbon Compounds*, Volumes 1–5 and Supplementals (Elsevier Science Publishers, 1989), *Organic Reactions*, Volumes 1–40 (John Wiley and Sons, 1991), *March's* Advanced Organic Chemistry, (John Wiley and Sons, 1992), and *Larock's* Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Compounds of Formula (I) where X is —S— can be prepared using General Synthetic Scheme 1.

General Synthetic Scheme 1

A specific synthetic example of this general scheme is illustrated in Synthetic Example 1.

Compounds where X is —CH₂— can be prepared using General Synthetic Scheme 2.

General Synthetic Scheme 2

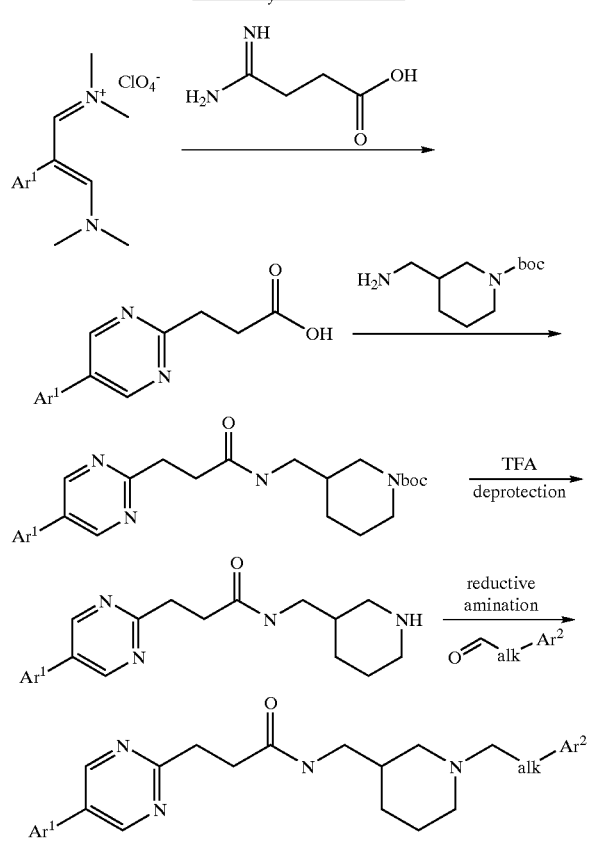

A specific synthetic example of this general scheme is illustrated in Synthetic Example 2.

Compounds where X is —O— can be prepared using General Synthetic Scheme 3.

General Synthetic Scheme 3

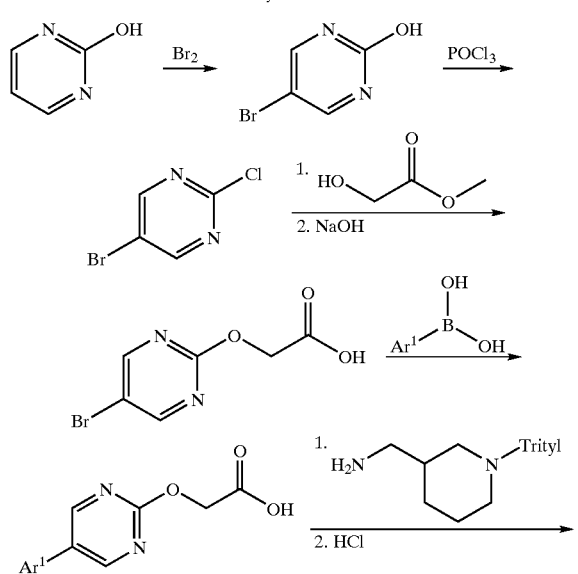

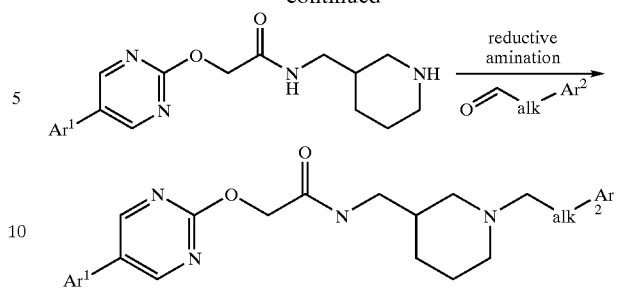

A specific synthetic example of this general scheme is illustrated in Synthetic Example 3.

Utility, Testing and Administration

General Utility

The compounds of the invention are CCR-3 receptor antagonists and inhibit eosinophil recruitment by CCR-3 chemokines such as RANTES, eotaxin, MCP-2, MCP-3, and MCP-4. Compounds of this invention and compositions containing them are useful in the treatment of eosinophil-induced diseases such as inflammatory or allergic diseases and including respiratory allergic diseases such as asthma, allergic rhinitis, hypersensitivity lung diseases, hypersensitivity pneumonitis, eosinophilic pneumonias (e.g., chronic eosinophilic pneumonia), inflammatory bowel diseases (e.g., Crohn's disease and ulcerative colitis), and psoriasis and inflammatory dermatoses such as dermatitis and eczema.

Additionally, it has recently been discovered that the CCR-3 receptor plays a role in the pathogenesis of Acquired Immune Deficiency Syndrome (AIDS). Accordingly, the compounds of this invention and compositions containing them are also useful in the treatment of AIDS.

Testing

The CCR-3 antagonistic activity of the compounds of this invention was measured by in vitro assays such as ligand binding and chemotaxis assays as described in more detail in Biological Examples 1, 2, and 3. In vivo activity is assayed in the Ovalbumin induced Asthma in Balb/c Mice Model as described in more detail in Biological Example 4.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.01–20 mg per kilogram body weight of the recipient per day; preferably about 0.1–10 mg/kg/day. Thus, for administration to a 70 kg person, the dosage range would most preferably be about 7 mg to 0.7 g per day.

In general, compounds of this invention will be administered as pharmaceutical compositions by any one of the following routes: oral, inhalation (e.g., intranasal or oral inhalation), or parenteral (e.g., intramuscular, intravenous, or subcutaneous) administration. A preferred manner of administration is oral using a convenient daily dosage regimen which can be adjusted according to the degree of affliction. Compositions can take the form of tablets, pills, capsules, semisolids, powders, sustained release formulations, solutions, suspensions, liposomes, elixirs, or any other appropriate compositions. Another preferred manner for administering compounds of this invention is inhalation. This is an effective means for delivering a therapeutic agent directly to the respiratory tract for the treatment of diseases such as asthma and other similar or related respiratory tract disorders (see U.S. Pat. No. 5,607,915).

The choice of formulation depends on various factors such as the mode of drug administration and the bioavailability of the drug substance. For delivery via inhalation the compound can be formulated as liquid solutions or suspensions, aerosol propellants or dry powder and loaded into a suitable dispenser for administration. There are three types of pharmaceutical inhalation devices—nebulizer inhalers, metered-dose inhalers (MDI), and dry powder inhalers (DPI). Nebulizer devices produce a stream of high velocity air that causes the therapeutic agents (which has been formulated in a liquid form) to spray as a mist which is carried into the patient's respiratory tract. MDI's typically have the formulation packaged with a compressed gas. Upon actuation, the device discharges a measured amount of therapeutic agent by compressed gas, thus affording a reliable method of administering a set amount of agent. DPI's administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to the patient with each actuation. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from glycerol, propylene glycol, water, ethanol and various oils, including those of petroleum, animal, vegetable, or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

For liposomal formulations of the drug for parenteral or oral delivery the drug and the lipids are dissolved in a suitable organic solvent e.g. tert-butanol, cyclohexane (1% ethanol). The solution is lypholized and the lipid mixture is suspended in an aqueous buffer and allowed to form a liposome. If necessary, the liposome size can be reduced by sonification. (see., Frank Szoka, Jr. and Demetrios Papahadjopoulos, "Comparative Properties and Methods of Preparation of Lipid Vesicles (Liposomes)", *Ann. Rev. Biophys. Bioeng.*, 9:467–508 (1980), and D. D. Lasic, "Novel Applications of Liposomes", *Trends in Biotech.*, 16:467–608, (1998))

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Formulation Example 1.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Synthetic Example 1

Synthesis of 2-[5-(3,4-Dimethoxy-phenyl)-pyrimidin-2-ylsulfanyl]-N-[1-(1H-indol-6-ylmethyl)-piperidin-3-ylmethyl]-acetamide

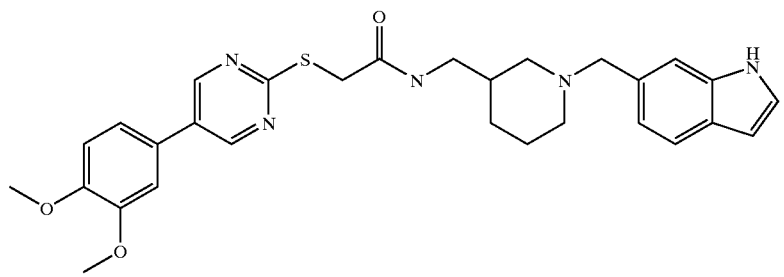
Scheme 1
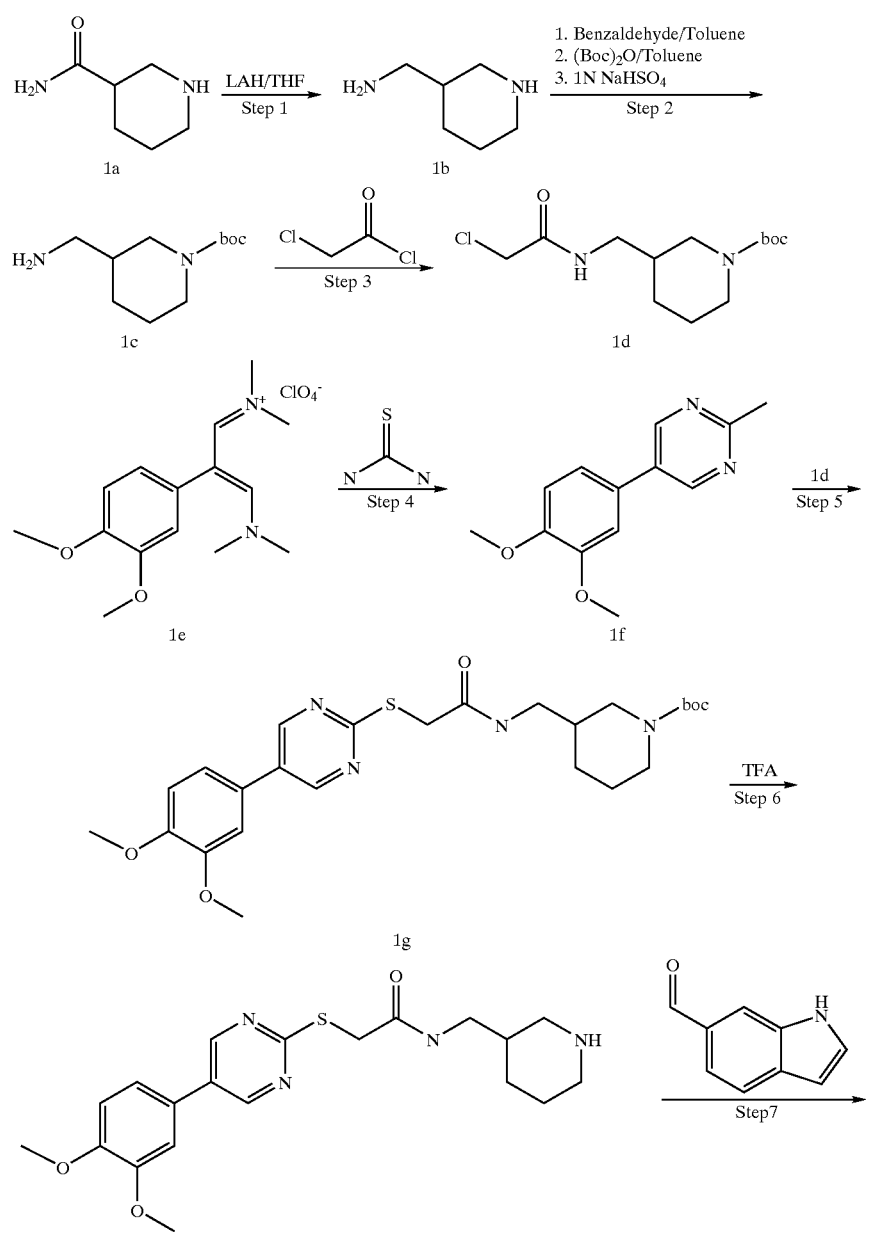

Step 1

Piperidine-3-carboxylic acid amide 1a (25 g, 0.195 mol) was added portionwise to a stirred solution of lithium aluminum hydride (14.8 g, 0.39 mol, 2.0 equiv) in dry THF (0.6 L). When the initial effervescence had subsided, the reaction was heated at reflux under $N_2$ at rt for 24 h. The reaction was quenched by dropwise addition of saturated sodium sulfate solution with stirring until no further effervescence was observed. The suspension was filtered through a celite plug, washed with THF (400 mL), and the filtrate concentrated under reduced pressure. The crude residue was distilled to yield pure product 1b as a colorless oil (12.4 g, 55%).

Step 2

Benzaldehyde (20.9 g, 197 mmol) was added to a solution of 3-aminomethylpiperidine 1b (22.5 g, 197 mmol) dissolved in toluene (anhydrous, 200 mL) in a 50 mL flask at rt under $N_2$. A Dean-Stark apparatus and condenser were fitted, the reaction vessel well lagged, and the reaction mixture heated at a strong reflux for 3 h. (4.9 ml of water was collected). The mixture was cooled to rt and di-tert-butyl dicarbonate (47.4 g, 217 mmol, 1.1 equiv) was added portion-wise and the resulting solution was stirred at rt overnight. The mixture was concentrated and the resulting residue diluted with 250 mL of 1M $NaHSO_4$. After stirring vigorously for no more than 2 h, the mixture was washed with ether to remove unwanted byproducts. The aqueous solution was then made strongly basic (pH 12) with NaOH and extracted thoroughly with ethyl acetate. The organic layer was washed with brine, dried with anhydrous $Na_2SO_4$, and concentrated to give 3-aminomethyl-piperidine-1-carboxylic acid tert-butyl ester 1c as a colorless oil (33.8 g, 80%), which was used directly without further purification.

Step 3

3-Aminomethyl-piperidine-1-carboxylic acid tert-butyl ester 1c (5.0 g, 23.4 mmol) in 20 mL $CH_2Cl_2$ was added dropwise to a cold (−10→0° C.) solution of chloroacetyl-chloride (2.8 mL, 35 mmol, 1.5 equiv) and diisopropylethylamine (6.1 mL, 35 mmol, 1.5 equiv) in 60 mL $CH_2Cl_2$ under $N_2$. After being left overnight (−10° C.→rt), the mixture was diluted with ethyl acetate and washed briefly with water and brine, dried ($Na_2SO_4$), and concentrated to give 3-[(2-chloroacetylamino)-methyl]-piperidine-1-carboxylic acid tert-butyl ester 1d as a dark brown oil. The crude product was used without further purification.

Step 4

The preparation of 5-(3,4-dimethoxy-phenyl)-pyrimidine-2-thiol was analogous to that described for similar analogues [Krecmerova, M.; Hrebabecky, H.; Masojidkova, M.; Holy, A. *Collect. Czech. Chem. Commun.* 1996, 61, 458]. A solution of sodium ethoxide (21 wt/vol, 9.25 mL, 25 mmol, 2.5 equiv) was added to a suspension of 2-(3,4-dimethoxyphenyl)trimethinium perchlorate 1e (3.62 g, 10 mmol) [Jutz, C.; Kirchlechner, R.; Seidel, H. *Chem. Ber.* 1969, 102, 2301] and thiourea (1.0 g, 13 mmol, 1.3 equiv) in absolute ethanol (100 mL). The mixture was stirred at rt for 30 min and then heated at reflux temperature for 2 h. The yellow suspension was cooled to rt, quenched with acetic acid (6 mL), and filtered. The solid was washed with water and cold ethanol and dried under high vacuum to give 5-(3,4-dimethoxy-phenyl)-pyrimidine-2-thiol 1f as a yellow solid (2.4 g, 97%).

Step 5

5-(3,4-Dimethoxy-phenyl)-pyrimidine-2-thiol 1f (0.75 g, 3 mmol) was added to a solution of the 2-chloroacetamide 1d (1.3 g, ~80% purity, ~3.6 mmol, obtained from step 3) and diisopropylethylamine (0.78 mL, 4.5 mmol, 1.5 equiv) in dry $CH_2Cl_2$. The resulting suspension was stirred at rt for about 2 h, at which time the reaction mixture became a dark brown solution and all the solid disappeared. The mixture was then concentrated and chromatographed on silica gel (ethyl acetate). The fractions containing the major product were combined and concentrated to an oily residue. Trituration of the oil with ether afforded 3-({2-[5-(3,4-dimethoxy-phenyl)-pyrimidin-2-ylsulfanyl]-acetylamino}-methyl)-piperidine-1-carboxylic acid tert-butyl ester 1g (0.83 g, 55%) as a dark brown solid.

Step 6

Anhydrous TFA (3 mL) was added to a solution of 3-({2-[5-(3,4-dimethoxy-phenyl)-pyrimidin-2-ylsulfanyl]-acetylamino}-methyl)-piperidine-1-carboxylic acid tert-butyl ester 1g (0.60 g, 1.20 mmol) in $CH_2Cl_2$ (10 mL) at rt. Gas evolution was apparent immediately upon addition of the acid. After 30 min the mixture was concentrated using a teflon dryvac system and was then further concentrated under high vacuum. LCMS analysis indicated complete and clean conversion to 2-[5-(3,4-dimethoxy-phenyl)-pyrimidin-2-ylsulfanyl]-N-piperidin-3-ylmethyl-acetamide 1h. Remaining traces of TFA did not affect subsequent steps.

Step 7

1H-indole-6-carbaldehyde (238 mg, 1.64 mmol, 1.36 equiv) [Moyer, Mikel P.; Shiurba, John F.; Rapoport, Henry; *J. Org. Chem.;* 1986, 51, 5106–5110] was added to the solution of the 2-[5-(3,4-dimethoxy-phenyl)-pyrimidin-2-ylsulfanyl]-N-piperidin-3-ylmethyl-acetamide 1h (TFA)n (1.20 mmol, obtained from step 6) and diisopropylethylamine (0.85 mL, 4.8 mmol, 4 equiv) in 50 mL dichloroethane. Sodium triacetoxyborohydride (0.47 g, 2.24 mmol, 1.8 equiv) was added to the solution and the resulting suspension was stirred vigorously overnight. Methanol (5 mL) was added to quench the reaction. The mixture was concentrated and the residue was diluted with ethyl acetate. The solution was poured into saturated $NaHCO_3$ solution (40 mL) and extracted with EtOAc. The combined organic phases were washed with brine, dried ($Na_2SO_4$), and concentrated. Chromatography on silica gel (10% methanol in chloroform) afforded 2-[5-(3,4-dimethoxy-phenyl)-pyrimidin-2-ylsulfanyl]-N-[1-(1H-indol-6-ylmethyl)-piperidin-3-ylmethyl]-acetamide (free base, 410 mg, 64%) as a light tan solid.

Proceeding as described above but substituting 1H-indole-6-carbaldehyde with 3,4-dibromobenzaldehyde gave N-[1-(3,4-dibromo-benzyl)-piperidin-3-ylmethyl]-2-[5-(3,4-dimethoxy-phenyl)-pyrimidin-2-ylsulfanyl]-acetamide.

Proceeding as described above but substituting 1H-indole-6-carbaldehyde with 3-(trifluoromethyl)-4-chlorobenzaldehyde gave N-[1-(4-chloro-3-trifluoromethyl-benzyl)-piperidin-3-ylmethyl]-2-[5-(3,4-dimethoxy-phenyl)-pyrimidin-2-ylsulfanyl]-acetamide.

Proceeding as described above but substituting 1H-indole-6-carbaldehyde with 3-chlorobenzaldehyde gave N-[1-(3-chloro-benzyl)-piperidin-3-ylmethyl]-2-[5-(3,4-dimethoxy-phenyl)-pyrimidin-2-ylsulfanyl]-acetamide.

Proceeding as described above but substituting 1H-indole-6-carbaldehyde with piperonal gave N-(1-benzo[1,3]dioxol-5-ylmethyl-piperidin-3-ylmethyl]-2-[5-(3,4-dimethoxy-phenyl)-pyrimidin-2-ylsulfanyl]-acetamide.

Proceeding as described above but substituting 1H-indole-6-carbaldehyde with 3,4-diflorobenzaldehyde gave N-[1-(3,4-difluoro-benzyl)-piperidin-3-ylmethyl]-2-[5-(3,4-dimethoxy-phenyl)-pyrimidin-2-ylsulfanyl]-acetamide.

Proceeding as described above but substituting 1H-indole-6-carbaldehyde with 4,5-dibromothiophene-2- carboxaldehyde gave N-[1-(4,5-dibromo-thiophen-2-ylmethyl)-piperidin-3-ylmethyl]-2-[5-(3,4-dimethoxy-phenyl)-pyrimidin-2-ylsulfanyl]-acetamide.

Proceeding as described above but substituting 1H-indole-6-carbaldehyde with 4,5-dichloro thiophene-2-carboxaldehyde [Profft, E.; Solf, G.; J. Prakt. Chem. 1964, 24, 38. And Sonnet, P. E.; J Med. Chem. 1972, 15, 97] gave N-[1-(4,5-dichloro-thiophen-2-ylmethyl)-piperidin-3-ylmethyl]-2-[5-(3,4-dimethoxy-phenyl)-pyrimidin-2-ylsulfanyl]-acetamide.

Proceeding as described above but substituting 1H-indole-6-carbaldehyde with indan-5-carbaldehyde [Hinkel; Ayling; Beynon; J. Chem. Soc. 1936, 339, 340] gave 2-[5-(3,4-dimethoxy-phenyl)-pyrimidin-2-ylsulfanyl]-N-(1-indan-5-ylmethyl-piperidin-3-ylmethyl)-acetamide.

Proceeding as described above but substituting 2-[5-(3,4-dimethoxy-phenyl)-pyrimidin-2-ylsulfanyl]-N-piperidin-3-ylmethyl-acetamide (TFA)n with 2-[5-(4-methoxy-phenyl)-pyrimidin-2-ylsulfanyl]-N-piperidin-3-ylmethyl-acetamide (TFA)n and substituting 1H-indole-6-carbaldehyde with 3,4-dichlorobenzaldehyde gave N-[1-(3,4-dichloro-benzyl)-piperidin-3-ylmethyl]-2-[5-(4-methoxy-phenyl)-pyrimidin-2-ylsulfanyl]-acetamide.

Proceeding as described above but substituting 2-[5-(3,4-dimethoxy-phenyl)-pyrimidin-2-ylsulfanyl]-N-piperidin-3-ylmethyl-acetamide (TFA)n with 2-[5-(4-methoxy-phenyl)-pyrimidin-2-ylsulfanyl]-N-piperidin-3-ylmethyl-acetamide (TFA)n and substituting 1H-indole-6-carbaldehyde with 2,3-dichlorobenzaldehyde gave N-[1-(2,3-dichloro-benzyl)-piperidin-3-ylmethyl]-2-[5-(4-methoxy-phenyl)-pyrimidin-2-ylsulfanyl]-acetamide.

Proceeding as described above but substituting 2-[5-(3,4-dimethoxy-phenyl)-pyrimidin-2-ylsulfanyl]-N-piperidin-3-ylmethyl-acetamide (TFA)n with 2-[5-(4-methoxy-phenyl)-pyrimidin-2-ylsulfanyl]-N-piperidin-3-ylmethyl-acetamide (TFA)n and substituting 1H-indole-6-carbaldehyde with piperonal gave N-(1-benzo[1,3]dioxol-5-ylmethyl-piperidin-3-ylmethyl)-2-[5-(4-methoxy-phenyl)-pyrimidin-2-ylsulfanyl]-acetamide.

Proceeding as described above but substituting 2-[5-(3,4-dimethoxy-phenyl)-pyrimidin-2-ylsulfanyl]-N-piperidin-3-ylmethyl-acetamide (TFA)n with 2-[5-(4-methoxy-phenyl)-pyrimidin-2-ylsulfanyl]-N-piperidin-3-ylmethyl-acetamide (TFA)n gave N-[1H-indol-6-ylmethyl)-piperidin-3-ylmethyl]-2-[5-(4-methoxy-phenyl)-pyrimidin-2-ylsulfanyl]-acetamide.

Synthetic Example 2

Synthesis of N-(1-(3,4-Dichloro-benzyl)-piperidine-3-ylmethyl)-3-(5-(3,4-dimethoxyphenyl)-pyrimidin-2-yl)-propionamide

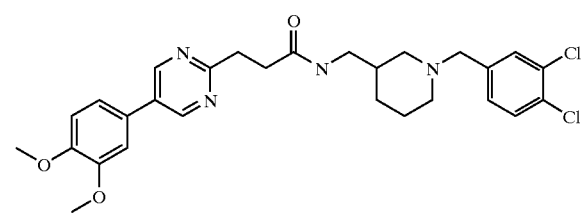

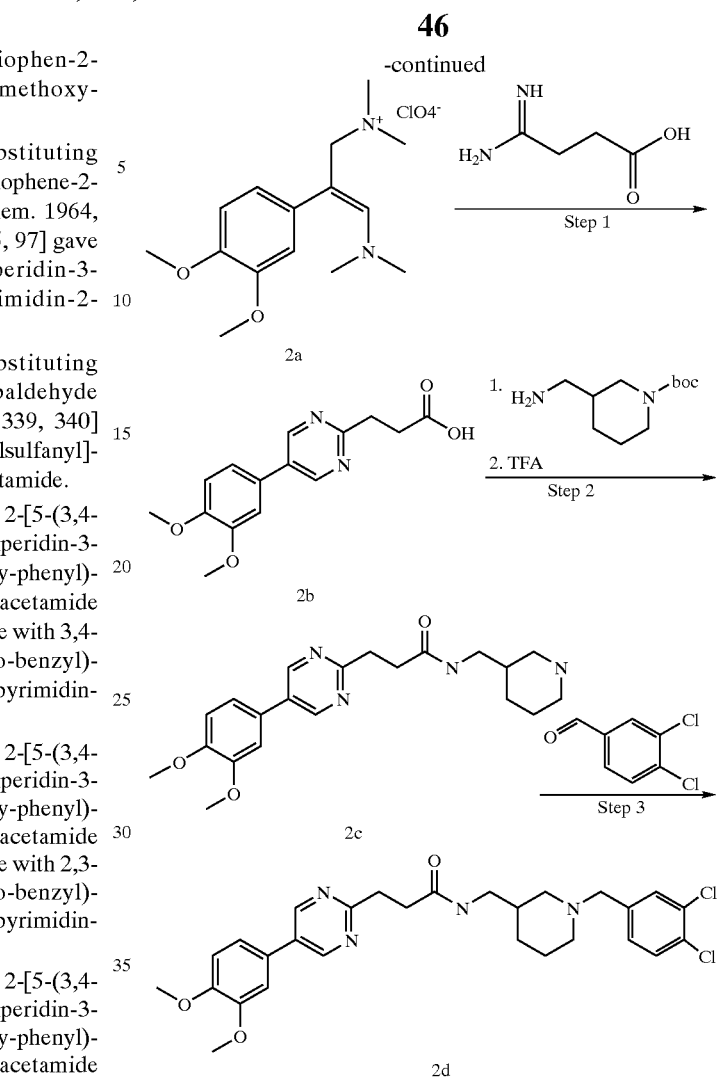

Step 1

A solution of sodium ethoxide (21% wt/vol in ethanol, 53 mL, 160 mmol, 3 equiv) was added in one portion to a suspension of 2-(3,4-dimethoxyphenyl)trimethinium perchlorate 2a (15.8 g, 44 mmol) [Jutz, C.; Kirchlechner, R.; Seidel, H. Chem. Ber. 1969, 102, 2301] and 4-amidinobutanoic acid mono HCl (8.0 g, 52.5 mmol, 1.2 equiv) [McElvain, S. M.; Schroeder, J. P. J. Am. Chem. Soc, 1949, 71, 40] in 200 mL of absolute ethanol. The mixture was heated at reflux temperature for 12 h, then cooled to rt. The suspension was concentrated, diluted with water, and washed with ether. The aqueous phase was then made acidic upon addition of excess a saturated citric acid solution, resulting in precipitation of the product. The precipitate was filtered, washed with water and briefly washed with cold methanol, then thoroughly washed with ether, and dried under high vacuum to yield 7.3 g (58%) of 3-(5-(3,4-dimethoxy-phenyl)-pyrimidin-2-yl)-propanoic acid 2b as an off-white solid.

Step 2

The mono HCl salt of EDC (0.86 g, 4.5 mmol, 1.5 equiv) was added to a suspension of 3-(5-(3,4-dimethoxy-phenyl)pyrimidin-2-yl)-propanoic acid (0.95 g, 3.3 mmol, 1.1 equiv), 3-aminomethyl-piperidine-1-carboxylic acid tert-butyl ester (0.64 g, 3.0 mmol), HOBT (0.61 g, 4.5 mmol, 1.5 equiv), and diisopropylethylamine (1.3 mL, 7. mmol, 2.5 equiv) in a 50 mL solvent (THF:DMF, 7:3). After stirring overnight at rt, the mixture was concentrated and the residue was dissolved in 50 mL ethyl acetate. The solution was poured into 50 mL of a saturated NaHCO$_3$ solution and extracted thoroughly with ethyl acetate. The combined organic layers were washed with brine and water, dried (Na$_2$SO$_4$), and concentrated. The residue was purified by flash chromatography (0→10% MeOH in CHCl$_3$). Clean fractions containing the desired product were combined and concentrated to give 3-({3-[5-(3,4-dimethoxy-phenyl)-pyrimidin-2-yl]-propionylamino}-methyl)-piperidine-1-carboxylic acid tert-butyl ester (1.22 g, 84%) as a dark brown solid. The solid was dissolved into CH$_2$Cl$_2$ (30 mL) and neat TFA (5 mL) added dropwise. After about 30 min, the solution was concentrated to an oil on the teflon dryvac, then under high vacuum. LCMS analysis indicated quantitative conversion to 3-[5-(3,4-dimethoxy-phenyl)-pyrimidin-2-yl]-N-piperidin-3-ylmethyl-propionamide 2c.

Step 3

Neat 3,4-dichlorobenzaldehyde (0.39 g, 2.2 mmol, 1.1 equiv) was added to a solution of 3-[5-(3,4-dimethoxy-phenyl)-pyrimidin-2-yl]-N-piperidin-3-ylmethyl-propionamide (TFA)$_n$ (2.0 mmol, obtained from step 2) and diisopropylethylamine (1.1 mL, 6.0 mmol, 3 equiv) in 50 mL dichloroethane. Sodium triacetoxyborohydride (699 mg, 3.3 mmol, 1.65 equiv) was added to the solution and the resulting suspension was stirred vigorously overnight. Methanol (5 mL) was added to quench the reaction. The mixture was concentrated and the residue was diluted with ethyl acetate. The solution was poured into a saturated NaHCO$_3$ solution (40 mL) and extracted with EtOAc. The combined organic phases were washed with brine, dried over Na$_2$SO$_4$, and concentrated. Chromatography on silica gel (10% methanol in chloroform) afforded N-(1-(3,4-dichloro-benzyl)-piperidin-3-ylmethyl)-3-(5-(3,4-dimethoxy-phenyl)-pyrimidin-2-yl)-propionamide 2d (free base, 720 mg, 66%) as a light yellow solid.

Proceeding as described above but substituting 3,4-dichlorobenzaldehyde with 3,4-dibromobenzaldehyde gave N-[1-(3,4-dibromo-benzyl)-piperidin-3-ylmethyl]-3-[5-(3,4-dimethoxy-phenyl)-pyrimidin-2-yl]-propionamide.

Proceeding as described above but substituting 3,4-dichlorobenzaldehyde with 3-(trifluoromethyl)-4-chlorobenzaldehyde gave N-[1-(4-chloro-3-trifluoromethyl-benzyl)-piperidin-3-ylmethyl]-3-[5-(3,4-dimethoxy-phenyl)-pyrimidin-2-yl]-propionamide.

Proceeding as described above but substituting 3,4-dichlorobenzaldehyde with 2,3-dichlorobenzaldehyde gave N-[1-(2,3-dichloro-benzyl)-piperidin-3-ylmethyl]-3-[5-(3,4-dimethoxy-phenyl)-pyrimidin-2-yl]-propionamide.

Proceeding as described above but substituting 3,4-dichlorobenzaldehyde with piperonal gave N-(1-benzo[1,3]dioxol-5-ylmethyl-piperidin-3-ylmethyl)-3-[5-(3,4-dimethoxy-phenyl)-pyrimidin-2-yl]-propionamide.

Proceeding as described above but substituting 3,4-dichlorobenzaldehyde with indan-5-carbaldehyde [Hinkel; Ayling; Beynon; J. Chem. Soc. 1936, 339, 340] gave 3-[5-(3,4-dimethoxy-phenyl)-pyrimidin-2-yl]-N-(1-indan-5-ylmethyl-piperidin-3-ylmethyl)-propionamide.

Proceeding as described above but substituting 3,4-dichlorobenzaldehyde with 4,5-dichloro-thiophene-2-carbaldehyde gave N-[1-(4,5-dichloro-thiophen-2-ylmethyl)-piperidin-3-ylmethyl]-3-[5-(3,4-dimethoxy-phenyl)-pyrimidin-2-yl]-propionamide.

Proceeding as described above but substituting 3,4-dichlorobenzaldehyde with 3,4-diflorobenzaldehyde gave N-[1-(3,4-difluoro-benzyl)-piperidin-3-ylmethyl]-3-[5-(3,4-dimethoxy-phenyl)-pyrimidin-2-yl]-propionamide.

Proceeding as described above but substituting 3-[5-(3,4-dimethoxy-phenyl)-pyrimidin-2-yl]-N-piperidin-3-ylmethyl-propionamide (TFA)n with 3-[5-(4-methoxy-phenyl)-pyrimidin-2-yl]-N-piperidin-3-ylmethyl-propionamide (TFA)n and substituting 3,4-dichlorobenzaldehyde with 2,3-dichlorobenzaldehyde gave N-[1-(2,3-dichloro-benzyl)-piperidin-3-ylmethyl]-3-[5-(4-methoxy-phenyl)-pyrimidin-2-yl]-propionamide.

Proceeding as described above but substituting 3-[5-(3,4-dimethoxy-phenyl)-pyrimidin-2-yl]-N-piperidin-3-ylmethyl-propionamide (TFA)n with 3-[5-(4-methoxy-phenyl)-pyrimidin-2-yl]-N-piperidin-3-ylmethyl-propionamide (TFA)n gave N-[1-(3,4-dichloro-benzyl)-piperidin-3-ylmethyl]-3-[5-(4-methoxy-phenyl)-pyrimidin-2-yl]-propionamide.

Proceeding as described above but substituting 3-[5-(3,4-dimethoxy-phenyl)-pyrimidin-2-yl]-N-piperidin-3-ylmethyl-propionamide (TFA)n with 3-[5-(4-methoxy-phenyl)-pyrimidin-2-yl]-N-piperidin-3-ylmethyl-propionamide (TFA)n and substituting 3,4-dichlorobenzaldehyde with piperonal gave N-(1-benzo[1,3]dioxol-5-ylmethyl-piperidin-3-ylmethyl)-3-[5-(4-methoxy-phenyl)-pyrimidin-2-yl]-propionamide.

Synthetic Example 3

Synthesis of: N-(1-(3,4-dichloro-benzyl)-piperidin-3-ylmethyl)-2-(5-(3,4-dimethoxy-phenyl)-pyrimidin-2-yloxy)-acetamide TFA salt (Scheme 3)

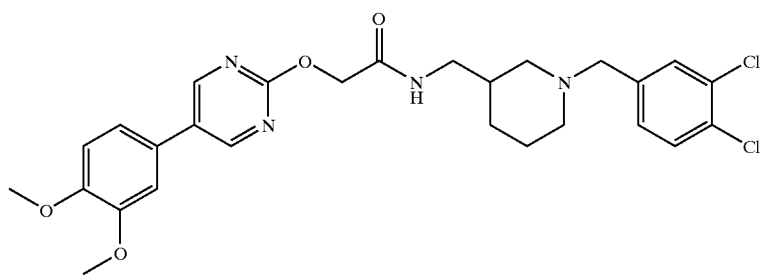
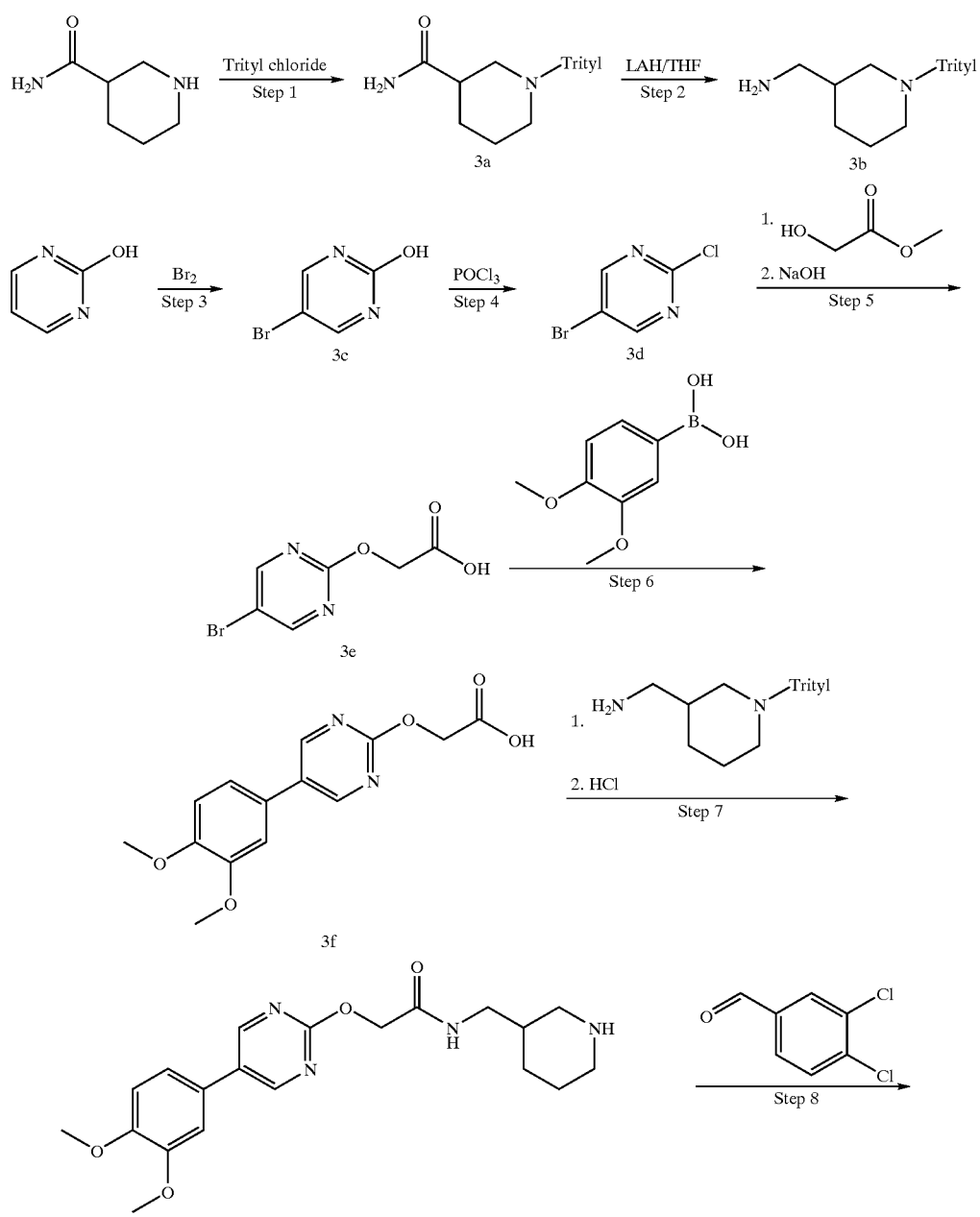
Scheme 3

Step 1

Trityl chloride (59.8 g, 0.215 mol) was added to a solution of piperidine-3-carboxylic acid amide (25 g, 0.20 mol) and triethylamine (54 mL, 0.39 mol, 2 equiv) in a mixture of THF and DMF (300 mL, 2:1) under $N_2$. After stirring overnight, the reaction was quenched with methanol (15 mL) and then concentrated. The residue was dissolved in 200 mL ethyl acetate and poured into 150 mL $NaHCO_3$. The aqueous layer was extracted with ethyl acetate. The combined organic layers were washed with brine and water, dried ($Na_2SO_4$), and concentrated. Chromatography on silica gel (10% methanol in chloroform) afforded N-1-trytylpiperidin-3-carboxylic acid amide 3a (60 g, 83%) as a yellow solid.

Step 2

N-1-tritylpiperidin-3-carboxylic acid amide 3a (30 g, 0.08 mol) was added portionwise to a stirred solution of lithium aluminium hydride (6.2 g, 0.16 mol, 2.0 equiv) in dry THF (600 mL). When the initial effervescence had subsided, the reaction was heated at reflux temperature under $N_2$ for 24 h. The reaction was quenched by dropwise addition of a saturate sodium sulphate solution with stirring until no further effervescence was observed. The suspension was filtered through a celite plug, eluting with THF (400 ml). The solvent was removed to afford 3-aminomethyl-1-tritylpiperidine 3b as a yellow foam (24.5 g, 85%).

Step 3

The procedure for the synthesis of 5-bromo-2-hydroxypyrimidine 3c is a variation of that published by Crosby and Berthold (*J. Chem. Soc.* 1960, 25, 1916). To a solution of 2-hydroxypyrimidine HCl (100 g, 0.75 mol) in $H_2O$ (1.2 L) $Br_2$ was added (135 g, 0.84 mol) slowly with stirring. The reaction mixture was continuously stirred for approximately 30 min. The solution was heated to 80° C. to drive of excess $Br_2$ and HBr. The solvent was concentrated further under vacuum and the residue recrystallized from 90% aqueous ethanol to afford 5-bromo-2-hydroxypyrimidine 3c (111 g, 84%).

Step 4

Phosphorus oxychloride (225 mL, 2.4 mol, 1.4 equiv) was added to a mixture of 5-bromo-2-hydroxypyrimidine (30 g, 0.17 mol) and dimethylaniline (7.5 mL) and the solution heated at reflux under $N_2$ for 4 h. The dark brown reaction mixture was cooled, poured over ice, and extracted with ether. The organic phase was washed with bicarbonate solution, dried ($Na_2SO_4$), and concentrated to afford 5-bromo-3-chloropyrimidine 3d (25 g, 75%) [Goodby, J. W.; Hird, M.; Lewis, R. A.; Toyne, K. J. *J. Chem. Soc., Chem. Commun.* 1996, 2719].

Step 5

The synthesis of (5-bromopyrimidin-2-yloxy)acetic acid 3e followed the protocol described for similar analogues [Coppola, G. M.; Hardtmann, G. E.; Huegi, B. S. *J. Heterocyl. Chem.* 1980, 17, 1479]. NaH (5.0 g, 60% dispersion in mineral oil, 124 mmol, 1.8 equiv) was washed twice with dry hexane under $N_2$, then added portionwise to a solution of methyl glycolate (9.4 g, 103 mmol, 1.5 equiv) in toluene (150 mL). The mixture was stirred at rt for 30 min, then 5-bromo-3-chloropyrimidine (13.3 g, 69 mmol) in toluene (50 mL) was added. The reaction mixture was heated at 60° C. overnight and concentrated. The residue was stirred rapidly with 1M NaOH (200 mL) for 30 min, washed with ether, then acidified to pH 3 with 4M HCl. The resulting precipitate was collected and washed with cold water. The filtrate was extracted further with ethyl acetate. The organic phase was washed with brine, dried ($Na_2SO_4$), and concentrated. The combined materials provided 10.3 g of (5-bromopyrimidin-2-yloxy)acetic acid 3e (64%).

Step 6

Solid 3,4-methoxyphenylboronic acid (1.22 g, 6.72 mmol, 1.05 equiv) was added to a solution of (5-bromopyrimidin-2-yloxy)acetic acid 3e (1.5 g, 6.4 mmol) in 1-propanol (50 mL). The suspension was stirred until all ingredients had dissolved. The resulting solution was treated with $Pd(OAc)_2$ (29 mg, 0.13 mmol, 0.02 equiv), $PPh_3$ (103 mg, 0.39 mmol, 0.06 equiv), 2M $Na_2CO_3$ (12 mL, 24 mmol, 3.8 equiv), and deionized water (10 mL). The mixture was heated at reflux under N2 for 1 h. Additional water (20 mL) was added and the $N_2$ inlet removed. After cooling to rt, the solution was acidified with 4M HCl. The resulting precipitate was filtered, washed with cold diluted HCl, and dried under vacuum to give 5-(3,4-dimethoxyphenyl)-pyrimidin-2-yloxy)acetic acid 3f as a brown solid (1.30 g, 70%).

Step 7

The mono HCl salt of EDC (0.66 g, 3.27 mmol, 1.5 equiv) was added to a suspension of 5-(3,4-dimethoxyphenyl) pyrimidin-2-yloxy)acetic acid 3f (0.66 g, 2.29 mmol, 1.05 equiv), 3-aminomethyl-1-tritylpiperidine 3b (0.78 g, 2.18 mmol), HOBT (0.46 g, 3.27 mmol, 1.5 equiv), a diisopropylethylamine (1.14 mL, 6.54 mmol, 3.0 equiv) in a 40 mL mixture solvent (THF:DMF, 7:3). After stirring overnight at rt, the mixture was concentrated and diluted with ethyl acetate. The solution was poured into 50 mL saturated $NaHCO_3$ solution and extracted with ethyl acetate. The combined organic layers were washed with brine, dried ($Na_2SO_4$), and concentrated. The residue was purified by flash chromatography (5–50% ethyl acetate in hexane). Clean fractions containing the desired product were combined and concentrated to give N-(1-tritylpiperidin-3-ylmethyl)-2-(5-(3,4-dimethoxyphenyl)pyrimidin-2-yloxy) acetamide (0.40 g, 29%) as a yellow oil. The oil product was dissolved into methanol (5 mL) and 4M HCl (20 mL) was added. After stirring about 1 h, the solution was concentrated to remove methanol and then additional 10 mL water was added. The aqueous solution was washed with ether, made strongly basic with 5M NaOH, and extracted with ethyl acetate. The combined organic layers were washed with brine and dried over $Na_2SO_4$. After removal of solvent, the desired product 2-[5-(3,4-dimethoxyphenyl)-pyrimidin-2-yloxy]-N-piperidin-3-ylmethyl-acetamide 3g was obtained as a yellow oil (172 mg, 70%). The product was made up as a stock solution to 4.5 mL with dichloroethane (0.10 mmol/mL).

Step 8

A stock solution of the 2-[5-(3,4-Ddimethoxy-phenyl)-pyrimidin-2-yloxy]-N-piperidin-3-ylmethyl-acetamide in dichloroethane (0.5 mL, 0.05 mmol) was added to solid 3,4-dichlorobenzaldehyde (10.5 mg, 0.06 mmol, 1.2 equiv). After the aldehyde was dissolved, $Na(OAc)_3BH$ (21 mg, 0.10 mmol, 2.0 equiv) was added and the resulting suspension was stirred vigorously overnight. The mixture was diluted with DMSO/methanol (1:1, 0.4 mL) and purified by reversed phase chromatography (Prep. LCMS). The fraction containing N-(1-(3,4-dichlorobenzyl)piperidin-3-ylmethyl)-2-(5-(3,4-dimethoxyphenyl)pyrimidin-2-yloxy)acetamide was concentrated to give a colorless oil (17 mg, 86%) as its TFA salt.

Proceeding as described above but substituting 3,4-dichlorobenzaldehyde with 2,3-dichlorobenzaldehyde gave N-[1-(2,3-dichloro-benzyl)-piperidin-3-ylmethyl]-2-[5-(3, 4-dimethoxy-phenyl)-pyrimidin-2-yloxy]-acetamide.

Proceeding as described above but substituting 2-[5-(3,4-dimethoxy-phenyl)-pyrimidin-2-yloxy]-N-piperidin-3-ylmethyl-acetamide (TFA)n with 2-[5-(4-methoxy-phenyl)-pyrimidin-2-yloxy]-N-piperidin-3-ylmethyl-acetamide (TFA)n gave N-[1-(3,4-dichloro-benzyl)-piperidin-3-ylmethyl]-2-[5-(4-methoxy-phenyl)-pyrimidin-2-yloxy]-acetamide.

Proceeding as described above but substituting 3,4-dichlorobenzaldehyde with piperonal gave N-(1-benzo[1,3]dioxol-5-ylmethyl-piperidin-3-ylmethyl)-2-[5-(3,4-dimethoxy-phenyl)-pyrimidin-2-yloxy]-acetamide.

Synthetic Example 4

Synthesis of:(±)-N-{1-[3-(4-Chloro-phenyl)-propionyl]-piperidin-3-ylmethyl}-2-[5-(3,4-dimethoxy-phenyl)-pyrimidin-2-ylsulfanyl]-acetamide

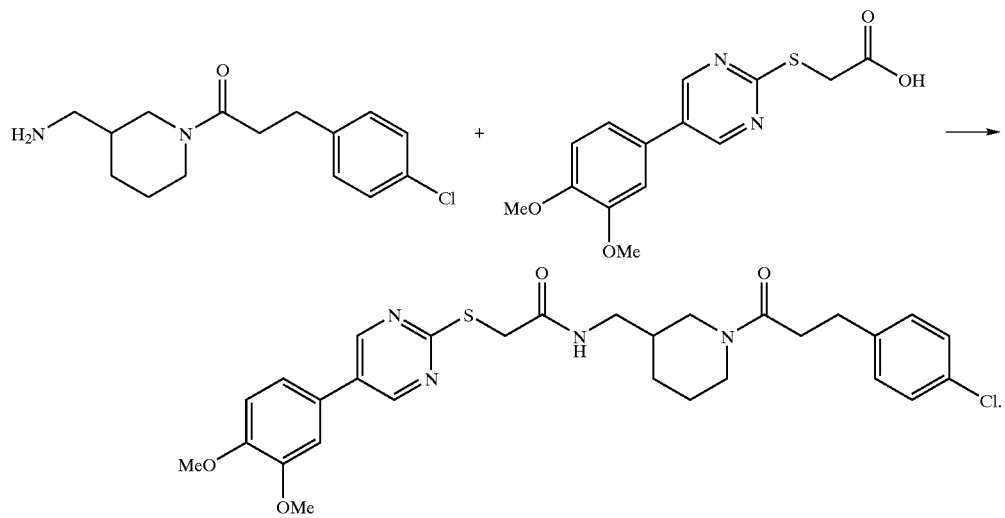

Step A:

A solution of (±)-1-(3-aminomethyl-piperidin-1-yl)-3-(4-chloro-phenyl)-propan-1-one (100 mg, 0.36 mmol), [5-(3,4-dimethoxy-phenyl)-pyrimidin-2-ylsulfanyl]-acetic acid (120 mg, 0.39 mmol), and 1-hydroxybenzotriazole hydrate (15 mg, 0.11 mmol) in $CH_2Cl_2$ (2 mL) at 0° C. was treated with 1-[3-(dimethylamino)propyl]-3-ethylcarbodiimide hydrochloride (103 mg, 0.54 mmol), allowed to warm to room temperature slowly, stirred for 5 h, and partitioned between $CH_2Cl_2$ and saturated $NaHCO_3$. The aqueous phase was extracted with $CH_2Cl_2$ and the extracts were washed with brine, dried ($Na_2SO_4$) and concentrated. Purification of the residue by preparative TLC with 10:0.95:0.05 $CH_2Cl_2$:MeOH:$NH_4OH$ gave the product (160 mg, 79%) as an orange solid: mp 61.3–71.7° C.; IR 3414 (br), 2930, 1637, 1519, 1398 cm$^{-1}$; $^1$H NMR CDCl$_3$ δ 1.08–1.57 (m, 4H), 2.30–3.09 (m, 7H), 3.68–3.90 (m, 11H), 4.05–4.30 (m, 1H), 7.21–7.33 (m, 6H), 8.18 (m, NH), 8.96 (d, 2H, J=16.2 Hz); MS m/z 569 (M+H)$^+$. Anal. ($C_{29}H_{33}ClN_4O_4S$) C, H, N.

Preparation of (±)-{1-[3-(4-chloro-phenyl)-propionyl]-piperidin-3-yl}-carbamic acid tert-butyl ester

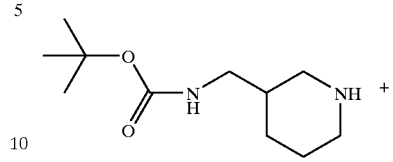

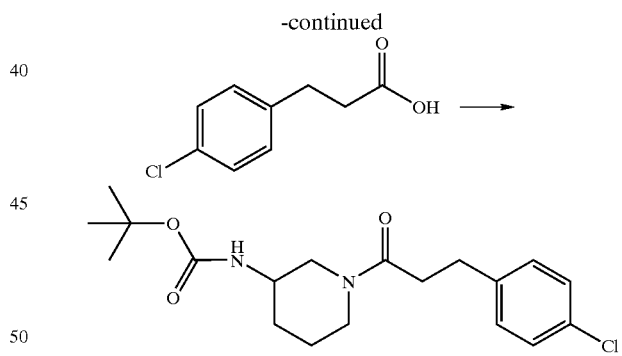

A solution of (±)-piperidin-3-ylmethyl-carbamic acid tert-butyl ester (550 mg, 2.57 mmol, AstaTech, Philadelphia, Pa., USA), 3-(4-chloro-phenyl)-propionic acid (569 mg, 3.08 mmol, Trans World Chemicals, Rockville, Md., USA) and 1-hydroxybenzotriazole hydrate (349 mg, 2.57 mmol) in $CH_2Cl_2$ (20 mL) was treated with 1-[3-(dimethylamino)propyl]-3-ethylcarbodiimide hydrochloride (739 mg, 3.85 mmol), stirred at room temperature overnight, and partitioned between $CH_2Cl_2$ and saturated $NaHCO_3$. The aqueous phase was extracted with $CH_2Cl_2$ and the extracts were washed with brine, dried ($Na_2SO_4$) and concentrated. Chromatography of the residue with 100:0.95:0.05–30:0.95:0.05 $CH_2Cl_2$:MeOH:$NH_4OH$ gave the product (870 mg, 89%) as a white foam: $^1$H NMR CDCl$_3$ δ 1.12–1.81 (m, 13H), 2.56–3.15 (m, 9H), 3.40–3.75 (m, 1H), 4.10–4.99 (m, 1H), 5.29 (m, 1H), 7.12–7.31 (m, 4H); MS m/z 381.1 (M+H)$^+$.

Step B:

Preparation of (±)-1-(3-aminomethyl-piperidin-1-yl)-3-(4-chloro-phenyl)-propan-1-one

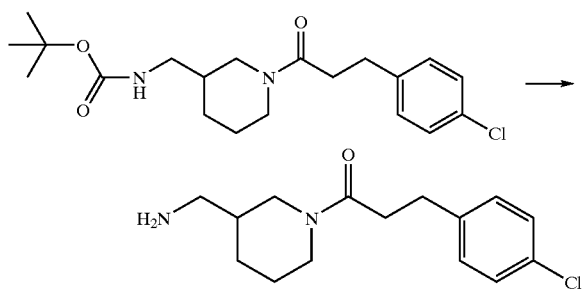

A solution of (±)-{1-[3-(4-chloro-phenyl)-propionyl]-piperidin-3-yl}-carbamic acid tert-butyl ester (870 mg, 2.28 mmol) in 10% HCl/MeOH (60 mL) was stirred at room temperature overnight and concentrated. The residue was partitioned between $CH_2Cl_2$ and saturated $NaHCO_3$. The aqueous phase was extracted with $CH_2Cl_2$ and the extracts were washed with brine, dried ($Na_2SO_4$) and concentrated to give 546 mg of the product as a colorless oil which was used directly in the next step: $^1H$ NMR $CDCl_3$ δ 1.10–1.86 (m, 4H), 2.31–3.08 (m, 10H), 3.45–3.82 (m, 1H), 4.33 (m, 1H), 5.29 (m, 1H), 7.11–7.28 (m, 4H).

Formulation Examples

The following are representative pharmaceutical formulations containing a compound of Formula (I).

Formulation Example 1

Tablet Formulation
The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation
The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation
The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation
The following ingredients are mixed to form an injectable formulation.

| Ingredient | Amount |
|---|---|
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

Liposomal Formulation
The following ingredients are mixed to form a liposomal formulation.

| Ingredient | Amount |
|---|---|
| compound of this invention | 10 mg |
| L-α-phosphatidylcholine | 150 mg |
| tert-butanol | 4 ml |

Freeze dry the sample and lyopholize overnight. Reconstitute the sample with 1 ml 0.9% saline solution. Liposome size can be reduced by sonication Biological Examples Biological Example 1

CCR-3 Receptor Binding Assay—in Vitro

The CCR-3 antagonistic activity of the compounds of the invention was determined by their ability to inhibit the binding of $^{125}I$ eotaxin to CCR-3 L1.2 transfectant cells (see Ponath, P. D. et al., *J. Exp. Med.*, Vol. 183, 2437–2448, (1996)).

The assay was performed in Costar 96-well polypropylene round bottom plates. Test compounds were dissolved in DMSO and then diluted with binding buffer (50 mM HEPES, 1 mM $CaCl_2$, 5 mM $MgCl_2$, 0.5% bovine serum albumin (BSA), 0.02% sodium azide, pH 7.24) such that the final DMSO concentration was 2%. Each well was filled with 25 μl of the test solution or only buffer with DMSO (control samples) followed by the addition of 25 μl of $^{125}I$-eotaxin (100 pmol) (NEX314, New England Nuclear, Boston, Mass.) and 1.5×10$^5$ of the CCR-3 L1.2 transfected cells in 25 μl binding buffer. The final reaction volume was 75 μl.

After incubating the reaction mixture for 1 h at room temperature, the reaction was terminated by filtering the reaction mixture through polyethylenimine treated Packard Unifilter GF/C filter plate (Packard, Chicago, Ill.). The filters were washed four times with ice cold wash buffer containing 10 mM HEPES and 0.5M sodium chloride (pH 7.2) and dried at 65° C. for approximately 10 min. 25 $\mu$l/well of Microscint-20™ scintillation fluid (Packard) was added and the radioactivity retained on the filters was determined by using the Packard TopCount™.

Compounds of this invention were active in this assay.

The $IC_{50}$ value (concentration of test compound required to reduce $^{125}$I-eotaxin binding to the CCR-3 L 1.2 transfected cells by 50%) for compounds in Table I of the invention was between 0.02 and 200 $\mu$M, preferably between 0.02 and 10 $\mu$M.

Biological Example 2

Inhibition of Eotaxin Mediated Chemotaxis of CCR-3 L1.2 Transfectant Cells—In Vitro Assay The CCR-3 antagonistic activity of the compounds of this invention is determined by measuring the inhibition of eotaxin mediated chemotaxis of the CCR-3 L1.2 transfectant cells, using a slight modification of the method described in Ponath, P. D. et al., *J. Clin. Invest.* 97: 604–612 (1996). The assay is performed in a 24-well chemotaxis plate (Costar Corp., Cambridge Mass.). CCR-3 L1.2 transfectant cells is grown in culture medium containing RPMI 1640, 10% Hyclone™ fetal calf serum, 55 mM 2-mercaptoethanol, and Geneticin 418 (0.8 mg/ml). 18–24 hours before the assay, the transfected cells are treated with n-butyric acid, at a final concentration of 5 mM/1×10$^6$ cells/ml, isolated, and resuspended at 1×10$^7$ cells/ml in assay medium containing equal parts of RPMI 1640 and Medium 199 (M 199) with 0.5% bovine serum albumin.

Human eotaxin suspended in phosphate buffered saline at 1 mg/ml is added to the bottom chamber in a final concentration of 100 nM. Transwell culture inserts (Costar Corp., Cambridge Mass.), having 3 micron pore size, are inserted into each well and L1.2 cells (1×10$^6$) are added to the top chamber in a final volume of 100 $\mu$l. Test compounds in DMSO are added both to the top and bottom chambers such that the final DMSO volume is 0.5%. The assay is performed against two sets of controls. The positive control contains cells with no test compound in the top chamber and only eotaxin in the lower chamber. The negative control contains cells with no test compound in the top chamber and neither eotaxin nor test compound in lower chamber. The plate is incubated at 37° C. After 4 h, the inserts are removed from the chambers and the cells that had migrated to the bottom chamber are counted by pipetting out 500 $\mu$l of the cell suspension from the lower chamber to 1.2 ml Cluster tubes (Costar) and counting them on a FACS for 30 sec.

Compounds of this invention are active in this assay.

Biological Example 3

Inhibition of Eotaxin Mediated Chemotaxis of Human Eosinophils—In Vitro Assay

The ability of compounds of the invention to inhibit eotaxin mediated chemotaxis of human eosinophils may be assessed using a slight modification of procedure described in Carr, M. W. et al., *Proc. Natl. Acad. Sci.* USA, 91: 3652–3656 (1994). Experiments are performed using 24 well chemotaxis plates (Costar Corp., Cambridge, Mass.). Eosinophils are isolated from blood using the procedure described in PCT Application, Publication No. WO 96/22371. The endothelial cell line ECV 304 obtained from European Collection of Animal Cell Cultures (Porton Down, Salisbury, U.K.) is used in this assay. Endothelial cells are cultured on 6.5 mm diameter Biocoat® Transwell tissue culture inserts (Costar Corp., Cambridge, Mass.) with a 3. $\mu$M pore size. Culture media for ECV 304 cells consists of M199, 10% Fetal Calf Serum, L-glutamine, and antibiotics. Assay media consists of equal parts RPMI 1640 and M199 and 0.5% BSA. Twenty-four hours before the assay 2×10$^5$ ECV 304 cells are plated on each insert of the 24-well chemotaxis plate and incubated at 37° C. 20 nM of eotaxin diluted in assay medium was added to the bottom chamber. The final volume in bottom chamber is 600 $\mu$l . The endothelial coated tissue culture inserts were inserted into each well. 10$^6$ eosinophil cells suspended in 100 $\mu$l assay buffer are added to the top chamber. Test compounds dissolved in DMSO are added to both top and bottom chambers such that the final DMSO volume in each well is 0.5%. The assay is performed against two sets of controls. The positive control contains cells in the top chamber and eotaxin in the lower chamber. The negative control contains cells in the top chamber and only assay buffer in the lower chamber. The plates are incubated at 37° C. in 5% $CO_2$/95% air for 1–1.5 h.

The cells that had migrate to the bottom chamber are counted using flow cytometry. 500 $\mu$l of the cell suspension from the lower chamber are placed in a tube and relative cell counts are obtained by acquiring events for a set time period of 30 seconds.

Compounds of this invention are active in this assay.

Biological Example 4

Inhibition of Eosinophil Influx into the Lungs of Ovalbumin Sensitized Balb/c Mice by CCR-3 Antagonist—In Vivo Assay The ability of the compounds of the invention to inhibit leukocyte infiltration into the lungs is determined by measuring the inhibition of eosinophil accumulation into the bronchioalveolar lavage (BAL) fluid of Ovalbumin (OA)-sensitized balb/c mice after antigen challenge by aerosol. Briefly, male balb/c mice weighing 20–25 g are sensitized with OA (10 $\mu$g in 0.2 ml aluminum hydroxide solution) intraperitoneally on days 1 and 14. After a week, the mice are divided into ten groups. Test compound, only vehicle (control group), or anti-eotaxin antibody (positive control group). These are administered either intraperitoneally, subcutaneously, or orally. After 1 h, the mice are placed in a Plexiglass box and exposed to OA aerosol generated by a PARISTAR™ nebulizer (PARI, Richmond, Va.) for 20 min. Mice which had not been sensitized or challenged are included as negative control. After 24 or 72 h, the mice are anesthetized (urethane, approx. 1 g/kg, i.p.), a tracheal cannula (PE 60 tubing) was inserted, and the lungs are lavaged four times with 0.3 ml PBS. The BAL fluid is transferred into plastic tubes and kept on ice. Total leukocytes in a 20 $\mu$l aliquot of the BAL fluid is determined by Coulter Counter™ (Coulter, Miami, Fla.). Differential leukocyte counts are made on Cytospin™ preparations which had been stained with a modified Wright's stain (Diff-Quick™) by light microscopy using standard morphological criteria.

Compounds of this invention are active in this assay.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound of Formula (I):

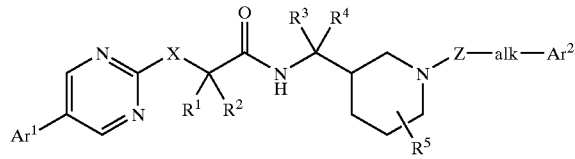

wherein:
Ar$^1$ is aryl;
Ar$^2$ is hydrogen, cycloalkyl, aryl or heteroaryl;
Z is —C(=O)— or a single bond;
R$^1$, R$^2$, R$^3$, R$^4$ and R$^5$ are independently hydrogen or alkyl optionally substituted with hydroxy;
alk is an alkylene chain of one to six carbon atoms;
X is —O—, —NR$^b$-(where R$^b$ is hydrogen or alkyl), (CR$^6$R$^7$)$_m$(where R$^6$ and R$^7$ are independently in each occurrence hydrogen or alkyl and m is an integer from 0 to 3), or —S(O)$_n$— (wherein n is an integer from 0 to 2);
or predrugs and pharmaceutically acceptable salts thereof.

2. The compound of claim 1, where Z is a single bond and R$^1$, R$^2$, R$^3$, R$^4$ and R$^5$ are hydrogen.

3. The compound of claim 2, wherein X is —S—.

4. The compound of claim 3, wherein alk is methylene.

5. The compound of claim 4, wherein Ar$^2$ is 3,4-dimethoxy-phenyl, 4-methoxy-phenyl, 3,4,5-trimethoxy-phenyl, or phenyl.

6. The compound of claim 4, wherein Ar$^2$ is 3,4-dichloro-phenyl, 2,3-dichloro-phenyl, 3,4-dibromo-phenyl, 3-chloro-4-trifluoromethyl-phenyl, 4-chloro-3trifluoromethyl-phenyl, benzo[1,3]dioxol-5-yl, indan-5-yl, or indol-6-yl.

7. The compound of claim 2, wherein X is —O.

8. The compound of claim 7, wherein alk is methylene.

9. The compound of claim 8, wherein Ar$^2$ is 3,4-dimethoxy-phenyl, 4-methoxy-phenyl, 3,4,5-trimethoxy-phenyl, or phenyl.

10. The compound of claim 8, wherein Ar$^2$ is 3,4-dichloro-phenyl, 2,3-dichloro-phenyl, 3,4-dibromo-phenyl, 3-chloro-4-trifluoromethyl-phenyl, 4-chloro-3-trifluoromethyl-phenyl, benzo[1,3]dioxol-5-yl, indan-5-yl, or indol-6-yl.

11. The compound of claim 2, wherein X is —(CR$^6$R$^7$)$_n$—.

12. The compound of claim 11, wherein alk is methylene.

13. The compound of claim 12, wherein Ar$^2$ is 3,4-dimethoxy-phenyl, 4-methoxy-phenyl, 3,4,5-trimethoxy-phenyl, or phenyl.

14. The compound of claim 12, wherein Ar$^2$ is 3,4-dichloro-phenyl, 2,3-dichloro-phenyl, 3,4-dibromo-phenyl, 3-chloro-4-trifluoromethyl-phenyl, 4-chloro-3-trifluoromethyl-phenyl, benzo[1,3]dioxol-5-yl, indan-5-yl, or indol-6-yl.

15. The compound of claim 2, wherein X is —NR$^b$—.

16. The compound of claim 15, wherein alk is methylene.

17. The compound of claim 16, wherein Ar$^2$ is 3,4-dimethoxy-phenyl, 4-methoxy-phenyl, 3,4,5-trimethoxy-phenyl, or phenyl.

18. The compound of claim 16, wherein Ar$^2$ is 3,4-dichloro-phenyl, 2,3-dichloro-phenyl, 3,4-dibromo-phenyl, 3-chloro-4-trifluoromethyl-phenyl, 4-chloro-3-trifluoromethyl-phenyl, benzo[1,3]dioxol-5-yl, indan-5-yl, or indol-6-yl.

19. Tho compound of claim 1, selected from the group consisting of:

2-[5-(3,4-Dimethoxy-phenyl)-pyrimidin-2-ylsulfanyl]-N-[1-(1H-indol-6-ylmethyl) piperidin-3-ylmethyl-acetamide;

N-[1-(3,4-Dichloro-benzyl)-piperidin-3-ylmethyl]-2-[5-(3,4-dimethoxy-phenyl)-pyrimidin-2-ylsulfanyl]-acetamide;

N-[1-(3,4-Dibromo-benzyl)-piperidin-3-ylmethyl]-2-[5-(3,4-dimethoxy-phenyl)-pyrimidin 2-ylsulfanyl]-acetamide;

N-[1-(4-Chloro-3-trifluoromethyl-benzyl)-piperidin-3-ylmethyl]-2-[5-(3,4 -dimethoxy-phenyl)-pyrimidin-2-ylsulfanyl]-acetamide;

N-[1-(3,4-Dichloro-benzyl)-piperidin-3-ylmethyl]-2-[5-(3,4-dimethoxy-phenyl)-pyrimidin-2-ylsulfanyl]-acetamide;

2-[5-(3,4-Dimethoxy-phenyl)-pyrimidin-2-ylsulfanyl]-N-[1-(1H-indol-6-ylmethyl)-piperidin-3-ylmethyl]-acetamide;

N-[1-(2,3-Dichloro-benzyl)-piperidin-3-ylmethyl]-2-[5-(3,4-dimethoxy-phenyl)-pyrimidin-2-ylsulfanyl]-acetamideacetamide;

N-[1-(3,4-Dibromo-benzyl)-piperidin-3-ylmethyl]-3-[5-(3,4-dimethoxy-phenyl)-pyrimidin-2-yl]-propionamide;

N-[1-(3,4-Dichloro-benzyl)-piperidin-3-ylmethyl]-3-[5-(3,4-dimethoxy-phenyl)-pyrimidin-2-yl]-propionamide;

N-[1-(3,4-Dichloro-benzyl)-piperidin-3-ylmethyl]-3-[5-(3,4-dimethoxy-phenyl)-pyrimidin-2-yl]-propionamide;

N-[1-(3-Chloro-benzyl)-piperidin-3-ylmethyl]2-[5-(3,4-dimethoxy-phenyl)-pyrimidin-2-ylsulfanyl]-acetamide;

N-[1-(4-Chloro-3-trifluoromethyl-benzyl)-piperidin-3-ylmethyl]-3-[5-(3,4-dimethoxy-phenyl)-pyrimidin-2-yl]-propionamide;

N-(1-Benzo[1,3]dioxol-5-ylmethyl-piperidin-3-ylmethyl] 2-[5-(3,4-dimethoxy-phenyl)-pyrimidin-2-ylsulfanyl]-acetamide;

N-[1-(3,4-Dichloro-benzyl)-piperidin-3-ylmethyl]-3-[5-(4-methoxy-phenyl)-pyrimidin-2-yl]-propionamide;

2-[5-(3,4-Dimethoxy-phenyl)-pyrimidin-2-ylsulfanyl]-N-(1-naphthalen-2-ylmethyl-piperidin-3-ylmethyl)-acetamide;

2-[5-(3,4-Dimethoxy-phenyl)-pyrimidin-2-ylsulfanyl]-N-(1-indan-5-ylmethyl-piperidin-3-ylmethyl)-acetamide;

N-[1-(4-Chloro-3-trifluoromethyl-benzyl)-piperidin-3-ylmethyl]-2-[5-(4-methoxy-phenyl)-pyrimidin-2-ylsulfanyl]-acetamide;

N-[1-(4,5-Dibromo-thiophen2-ylmethyl)-piperidin-3-ylmethyl]-2-[5-(3,4-dimethoxy-phenyl)-pyrimidin-2-ylsulfanyl]-acetamide;

N-[1-(4,5-Dichloro-thiophen-2-ylmethyl)-piperidin-3-ylmethyl]-2-[5-(3,4-dimethoxy-phenyl)-pyrimidin-2-ylsulfanyl]-acetamide;

N-{1-[3-(4-Chloro-phenyl)-propionyl]-piperidin-3-ylmethyl}-2-[5-(3,4-dimethoxy-phenyl)-pyrimidin-2-ylsulfanyl]-acetamide;

N-(1-Cyclopentylmethyl-piperidin-3-ylmethyl)-2-[4-(4,5-dimethoxy-pyrimidin-2-yl)-phenylsulfanyl]-acetamide;

N-[1-(2-Cyclopentyl-ethyl)-piperidin-3-ylmethyl]-2-[4-(4,5-dimethoxy-pyrimidin-2-yl)-phenylsulfanyl]-acetamide;

N-(1-Cyclohexylmethyl-piperidin-3-ylmethyl)-2-[4-(4,5-dimethoxy-pyrimidin-2-yl)-phenylsulfanyl]-acetamide;

and N-[1-(2-Cyclohexy-ethyl)-piperidin-3-ylmethyl]-2-[4-(4,5-dimethoxy-pyrimidin-2-yl)-phenylsulfanyl]-acetamide.

20. A pharmaceutical composition comprising a therapeutically effective amount of a compound of claim 1 and a pharmaceutically acceptable excipient.

21. A method of treatment of asthma, in a mammal comprising administration to the mammal of a pharmaceutical composition comprising a therapeutically effective amount of a compound of claim 1 and a pharmaceutically acceptable excipient.

22. A process for preparing a compound of claim 2 which comprises reacting a compound of formula d:

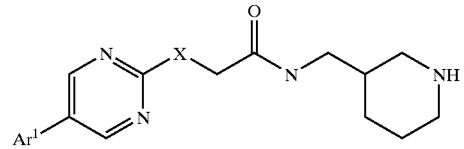

wherein $Ar^1$ and X are as described in claim 1, with a compound of formula OHC $Ar^2$ wherein $Ar^2$ is as described in claim 1, under reductive amination conditions, to prepare a compound of Formula (I):

(I)

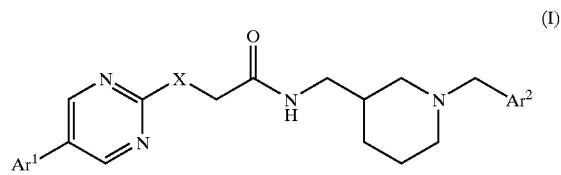

wherein $Ar^1$, X, and $Ar^2$ are as described in claim 1.

* * * * *